United States Patent
Domany et al.

(10) Patent No.: US 6,965,831 B2
(45) Date of Patent: Nov. 15, 2005

(54) COUPLED TWO-WAY CLUSTERING ANALYSIS OF DATA

(75) Inventors: Eytan Domany, Rehovot (IL); Gad Getz, Haifa (IL); Erel Levine, Tel Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 228 days.

(21) Appl. No.: 10/220,702

(22) PCT Filed: Mar. 9, 2001

(86) PCT No.: PCT/IL01/00228

§ 371 (c)(1),
(2), (4) Date: Sep. 5, 2002

(87) PCT Pub. No.: WO01/67061

PCT Pub. Date: Sep. 13, 2001

(65) Prior Publication Data

US 2003/0059818 A1 Mar. 27, 2003

(30) Foreign Application Priority Data

Mar. 9, 2000 (IL) .................................................. 134994

(51) Int. Cl.[7] .............................................. G06F 19/00
(52) U.S. Cl. .......................................... 702/19; 702/20
(58) Field of Search ..................................... 702/19, 20

(56) References Cited

U.S. PATENT DOCUMENTS 6,021,383 A * 2/2000 Domany et al. ............ 702/181

OTHER PUBLICATIONS te Poele et al. RNA synthesis block by 5,6–dichloro–1–beta–D–ribofuranosylbenzimidazole (DRB) triggers p53–dependent apoptosis in human colon carcinoma cells. Oncogene vol. 18, pp. 5765–5772 (1999).*

J. L. DeRisi, VR Iyer and PO Brown. Exploring the metabolic and genetic control of gene expression on a genomic scale. *Science*, 278:680–686, 1997.

U. Alon et al. Broad patterns of gene expression revealed by clustering analysis of tumor and normal colon tissues probed by oligonucleotide arrays. *PNAS*, 96:6745–6750, 1999.

M.B. Eisen et al. Cluster analysis and display of genome–wide expression patterns. *PNAS*, 95:14683–14686, 1998.

T.R. Golub et al. Molecular classification of cancer: Class discovery and class prediction by gene expression monitoring. *Science*, 286:531–537, 1999.

C.M. Perou et al. Distinctive gene expression patterns in human mammary epithelial cells and breast cancers. *PNAS*, 96:9212–9217, 1999.

E.S. Lander. Array of hope. *Nature Genetics*, 21:3–4, 1999.

M.Q. Zhang. Promoter analysis of co–regulated genes in the yeast genome. *Comput. Chem.*, 23:233–250, 1999.

M. Blatt et al. Super–paramagnetic clustering of data. *Physical Review Letters*, 76:3251–3254, 1996.

E. Domany. Super–paramagnetic clustering of data–the definitive solution of an ill–posed problem. *Physica A*, 263:158–169, 1999.

G. Getz et al. Super–paramagnetic clustering of yeast gene expression profiles. *Physica A*, 279 (2000) 457–464.

G. Getz et al. Coupled two way clustering of gene microarray dataPNAS, Oct. 24, 2000, vol. 97, No. 22, pp 12079–12084.

M. Blatt et al. Data clustering using a model granular magnet. *Neural Computation*, 9:1805–1842, 1997.

S. Wang and RH Swendsen. Cluster Monte–Carlo Algorithms. *Physica A.*, 167:565–579, 1990.

M. Schena et al. Parallel human genome analysis: microarray–based expression monitoring of 1000 genes. *PNAS*, 93:10614–10619, 1996.

Califano, et al., Analysis of Gene Expression Microarrays for Phenotype Classification, Proc. Int. Conf. Intell. Syst. Mol. Biol. (2000) vol. 8, pp. 75–85.

Y. Cheng et al., Biclustering of Expression Data, Proc. Int. Conf. Intell. Syst. Mol. Biol. (2000) vol. 8, pp. 93–103.

* cited by examiner

*Primary Examiner*—John S. Brusca
(74) *Attorney, Agent, or Firm*—G.E. Ehrlich (1995) Ltd.

(57) ABSTRACT

A novel coupled two-way clustering approach to gene microarray data analysis, for identifying subsets of the genes and samples, such that when one of these items is used to cluster the other, stable and significant partitions emerge. The method of the present invention preferably uses iterative clustering in order to execute this search in an efficient way. This approach is especially suitable for gene microarray data, where the contributions of a variety of biological mechanisms to the gene expression levels are entangled in a large body of experimental data. The method of the present invention was applied to two gene microarray data sets, on colon cancer and leukemia. By identifying relevant subsets of the data and focusing on these subsets, partitions and correlations were found that were masked and hidden when the full data set was used in the analysis.

27 Claims, 15 Drawing Sheets

Step 1. Initialization

1a. Let $v_0^g$ be the cluster of all genes, and $v_0^s$ be the cluster of all samples.

1b. Initialize sets of gene clusters, $V^g$, and sample clusters, $V^s$, such that $V^g = \{v_0^g\}$ and $V^s = \{v_0^s\}$.

1c. Add each known class of genes as a member of $V^g$, and each known class of samples as a member of $V^s$.

1d. Define a new set $W = \emptyset$. This set is needed to keep track of clustering analyses that have already been performed.

Step 2. For each pair $(v^g, v^s) \in (V^g \times V^s) \setminus W$:

2a. Apply the clustering algorithm on the genes of $v^g$ using the samples of $v^s$ as its features and vice versa.

2b. Add all the robust gene clusters generated by Step 2a to $V^g$, and all the robust sample clusters to $V^s$.

2c. Add $(v^g, v^s)$ to $W$.

Step 3. For each new robust cluster $u$ in either $V^g$ or $V^s$ define and store a pair of labels $P_u = (u_o, u_f)$. Of these, $u_o$ is the cluster of objects which were clustered to find $u$, and $u_f$ is the cluster of features used in that clustering.

Step 4. Repeat Step 2 until no new clusters are added to either $V^g$ or $V^s$.

Fig. 1

COUPLED TWO-WAY CLUSTERING ANALYSIS OF DATA

RELATED PATENT APPLICATION

This application is a National Phase Application of PCT/IL01/00228 filed Mar. 9, 2001 which claims priority from Israel Patent Application No. 134994 filed Mar. 9, 2000 which is still pending.

FIELD OF THE INVENTION

The present invention is of a method for analyzing large amounts of data through iterative clustering, and in particular, of such a method which is useful for the analysis of gene microarray data.

BACKGROUND OF THE INVENTION

DNA microarray technologies have enabled the expression levels of thousands of genes during various cellular processes to be monitored simultaneously [1, 2]. In a typical experiment expression levels of thousands of genes are recorded over a few tens of different samples [3, 5, 6]. By "sample", it is meant any kind of living matter that is being tested, such as different tissues [3], cell populations collected at different times [4] and so forth. Hence arrays that contain $10^5$–$10^6$ measurements must be analyzed, thereby giving rise to a new computational challenge: to make sense of such massive amounts of expression data [7, 8].

The aims of such analyses are typically to (a) identify cellular processes which affect the gene expression pattern; (b) search for different phases of these processes, by grouping the samples into clusters which share an expression pattern; (c) find genes which differentiate between these clusters, and hence take part in the relevant biological process and (d) explain the role these genes play in the process.

The sizes of the datasets and their complexity call for multi-variant clustering techniques which are essential for extracting correlated patterns from the swarm of data points in multidimensional space. The aim of clustering is to identify the natural classes present in a set of N data points, or objects, each one represented by means of D different measuredfeatures. That is, the data can be viewed as N points in a D dimensional space. The aim of clustering algorithms is to reveal the structure of this cloud of points, for example, to determine whether the data consists of a single cloud or several clouds, or whether the constituent components have any internal structure, revealed when the data are viewed with higher resolution. Under most circumstances the data points must be partitioned into clusters; it makes no sense to try and divide the features which characterize the data points into classes.

The situation with gene microarray data is different, in that clustering analysis can be performed in two ways. The first views the $n_s$ samples as the N objects to be clustered, with the $n_g$ genes' levels of expression in a particular sample playing the role of the features, that represent that sample as a point in a $D=n_g$ dimensional space. The different phases of a cellular process emerge from grouping together samples with similar or related expression profiles. The other, not less natural way looks for clusters of genes that act correlatively on the different samples. This view considers the $N=n_g$ genes as the objects to be clustered, each represented by its expression profile, as measured over all the samples, as a point in a $D=n_s$ dimensional space.

Gene microarray data are special in that both ways of looking at them have meaning and are of interest. Having realized this, Eisen et al and Alon et al applied such two-way clustering to data from experiments on yeast cell cycle [4] and colon cancer [3]. However, they clustered first the samples and then the genes completely independently, with no coupling at all between the two clustering procedures. In principle the two clustering operations could have been carried out in different places at different times; the results of one operation were not allowed to affect the other.

The current approach in the literature is to cluster the samples on the basis of as many genes as possible (usually the number used is limited by eliminating samples with the weakest signals). Similarly, when clustering genes, there is a tendency to rely on features accumulated from as many samples (even taken from different experiments! [4]) as possible. The philosophy behind this approach may be termed "holistic", as it attempts to extract information from the larger, overall, complete picture.

However, this approach clearly has a number of disadvantages. First, large amounts of data must be analyzed, which may require extensive resources, whether in human work hours, computational power or experimental procedures. Second, the signal-to-noise ratio may be quite poor with this approach, given the emphasis on analyzing the overall picture. Third, the actual points of interest may be obscured in the larger sets of data to analyze. All of these drawbacks clearly render currently available clustering techniques both less effective and less robust.

SUMMARY OF THE INVENTION

The background art does not teach or suggest a method for coupled two-way clustering analysis, which enables structural features to be derived through simultaneous usage of two sets of differentiating characteristics. Instead, the background art focuses on clustering analyses with a single set of differentiating features, which are not connected to each other. Thus, even if such a clustering-process is performed more than once according to the background art methods, the lack of connection between the features used for the clustering analysis significantly lowers the utility and strength of the resulting analyses.

There is therefore an unmet need for, and it would be useful to have, a method for clustering analysis which couples different sets of features for greater power in the resultant analysis, and which also is performed iteratively, in order to obtain coupled clustering analysis, particularly for the analysis of massive data sets, such as gene expression data for example.

For example, a first plurality of items, such as genes, can optionally be used to partition a second plurality of items, such as the samples that are analyzed, and vice versa. This ability to partition each of two separate groups of items according to the other group can be described as the "two-way" aspect of the method of the present invention. However, the "coupled" aspect of the method of the present invention particularly differentiates the present method from other background art methods. This "coupled" aspect can be generally described as follows: first, discover a subgroup of the first plurality of items, such as a subgroup of genes. Of course any other subgroup of a plurality of items which are linked according to some relationship through the data could be used. Second, use this subgroup of genes to partition the samples, or more generally, use the subgroup of the first group of items to partition the second group of items or any subgroup of it. The advantage of the "coupled" aspect of the method of the present invention is that the present invention can uncover interactions/partitions which would otherwise be lost in the noise of the overall data.

The combination enables the combinatorial search space to be much more effectively examined.

The method of the present invention can optionally be implemented as a software program for execution on any suitable type of computer. Regardless of the implementation, the functional steps performed by the method could be described as a plurality of instructions performed by a data processor.

According to the present invention there is provided a method for separating a first plurality of objects and a second plurality of objects into at least two groups, the method being performed by a data processor, the method comprising: dividing the first plurality of objects into a first plurality of object subsets; and partitioning the second plurality of objects according to at least one of the first plurality of object subsets to form at least two groups of the second plurality of objects.

However, it should be noted that the phrase "plurality of objects is separated to at least two groups" is not intended to be limiting in any way, as optionally the objects may not in fact separate into a plurality of groups, if no "natural" separation exists. The optional lack of separation of the plurality of objects, depending upon the information which is used to attempt to cluster or partition these objects, is actually an advantage of the method of the present invention, since it enables the lack of natural subgroups to be detected. By contrast, other methods in the background art always break data into a plurality of subgroups. Thus, the method of the present invention does not attempt to artefactually decompose a plurality of objects into subgroups, thereby giving a false or inaccurate result. For the purposes of clarity, the following discussion mentions separating the plurality of objects into a plurality of subgroups, it being understood that this description does not limit the present invention to the possibility that such a plurality of subgroups is always created by the method of the present invention, but instead also encompasses the possibility that no such subgroups are created.

Preferably, the method further comprises: partitioning at least a portion of the first plurality of objects according to at least one group of the second plurality of objects to form a plurality of subset groups of the first plurality of objects. More preferably, said at least a portion of the first plurality of objects is the entirety of the first plurality of objects. Alternatively, said at least a portion of the first plurality of objects is at least one subgroup of the first plurality of objects.

Optionally, each of the first plurality of objects is characterized according to at least one feature, and the division of the first plurality of objects is performed by: applying a clustering algorithm on the first plurality of objects according to said at least one feature to form a plurality of object subsets; and detecting at least one robust cluster from said plurality of object subsets. Preferably, said clustering algorithm is the superparamagnetic clustering algorithm.

Optionally, the method is repeated until no additional subgroups are detected. Preferably, no additional subgroups are detected for both the first plurality of objects and the second plurality of objects.

According to preferred embodiments of the present invention, the process of partitioning at least a portion of the first plurality of objects according to at least one group of the second plurality of objects is performed by partitioning a plurality of subset groups of the first plurality of objects according to a known classification.

According to other preferred embodiments of the present invention, the method further comprises analyzing each group of said at least two groups of the second plurality of objects by comparing said group of said at least two groups of the second plurality of objects to an entirety of the second plurality of objects to determine if said group is differentiated from the second plurality of objects.

According to still other preferred embodiments of the present invention, the method further comprises: analyzing each subset group of the first plurality of objects by comparing said subset group of the first plurality of objects to an entirety of the first plurality of objects to determine if said subset group is differentiated from the first plurality of objects. Preferably, the analysis is performed according to a statistical test for similarity. More preferably, the first plurality of objects is normalized before being divided. Alternatively or additionally, the second plurality of objects is normalized before being partitioned.

According to yet other preferred embodiments of the present invention, the first plurality of objects are genes and the second plurality of objects are samples for being analyzed according to a characteristic of said genes. Preferably, said samples are characterized according to expression levels of said genes. Optionally, said genes forming a cluster characterize a pathological state of a plurality of subjects, said samples being obtained from said plurality of subjects. Also optionally, said genes forming a cluster participate together in a biological process.

According to a preferred embodiment of the present invention, said genes are characteristic of samples taken from subjects having a cancerous condition. More preferably, at least one characteristic of said genes partitions said samples according to a type of cancer in said cancerous condition. Most preferably, said at least one characteristic of said genes is an expression profile of said genes. Also most preferably, said expression profile is determined as an expression matrix, such that the division of said samples into subgroups according to said expression profile for said genes is performed with said expression matrix.

Optionally, said at least one characteristic of said genes is an effect of treatment on said subjects.

According to still another embodiment of the present invention, the first plurality of objects are keywords and the second plurality of objects are documents containing said keywords.

According to another embodiment of the present invention, there is provided a method for separating at least one of a first plurality of objects and a second plurality of objects into at least two groups if a natural separation exists within at least one of the first plurality of objects and of the second plurality of objects, each of the first plurality of objects being related to at least one of the second plurality of objects, the method being performed by a data processor, the method comprising: dividing the first plurality of objects into a first plurality of object subsets; and partitioning the second plurality of objects according to at least one of said first plurality of object subjects to form at least two groups of the second plurality of objects.

According to yet another embodiment of the present invention, there is provided a method for analyzing data, available in the form of an array of numbers, wherein each row of the array represents measurements of the values taken by a particular attribute over several samples and each column represents the measurements of the various attributes taken for a particular sample.

Preferably, for the analysis of gene expression data taken from several tissues, the attributes are different genes for which expression levels were measured and the samples are human tissues or other biological material for which the expression levels of the genes have been determined.

More preferably, the method further comprises performing cluster analysis in two ways, over the samples and over the genes, wherein the two ways of clustering are coupled: each cluster of genes constitutes a probe which is used to cluster any group of samples, and vice versa. Most preferably, the method is iterative and whenever stable clusters are generated, they are used to further search for partitions (clusters) in the other dimension.

Optionally, gene clusters are used to look for partitions of tissues and tissue clusters are used to look for correlated clusters of genes. Also optionally, the method is used in conjunction with any clustering algorithm. Preferably, the method is used in conjunction with the superparamagnetic clustering algorithm. More preferably, the method uses a measure for the stability of clusters and identification of said stable clusters narrows significantly the groups (clusters) that are to be tested as probes.

Optionally, the method yields clusters of genes of correlated expression profiles that may participate in the same biological process. Preferably, said groups of genes relate to administration of pharmaceutical drugs, or differentiate one type of cancer from another, or reflect the change of experimental protocol in a colon-cancer treatment. More preferably, said method identifies tissues of groups of patients, or tissues subjected to different experimental protocols, or identifies different types of cancer. Most preferably, said method identifies different types of leukemia.

According to yet another embodiment of the present invention, there is provided an apparatus for carrying out a method according to any of the above embodiments.

BRIEF DESCRIPTION OF THE DRAWINGS

The invention is herein described, by way of example only, with reference to the accompanying drawings, wherein:

FIG. 1 is a flowchart of an exemplary coupled two-way clustering method according to the present invention. The input of the algorithm is the full expression matrix. The output is a set $V^g$ of stable gene clusters and a set $V^s$ of stable sample clusters. For each stable cluster u, found in a clustering operation, the clusters which provided the objects and those that served as the features for this operation are stored as a label $P_u$.

DESCRIPTION OF THE PREFERRED EMBODIMENTS

Figure 2:
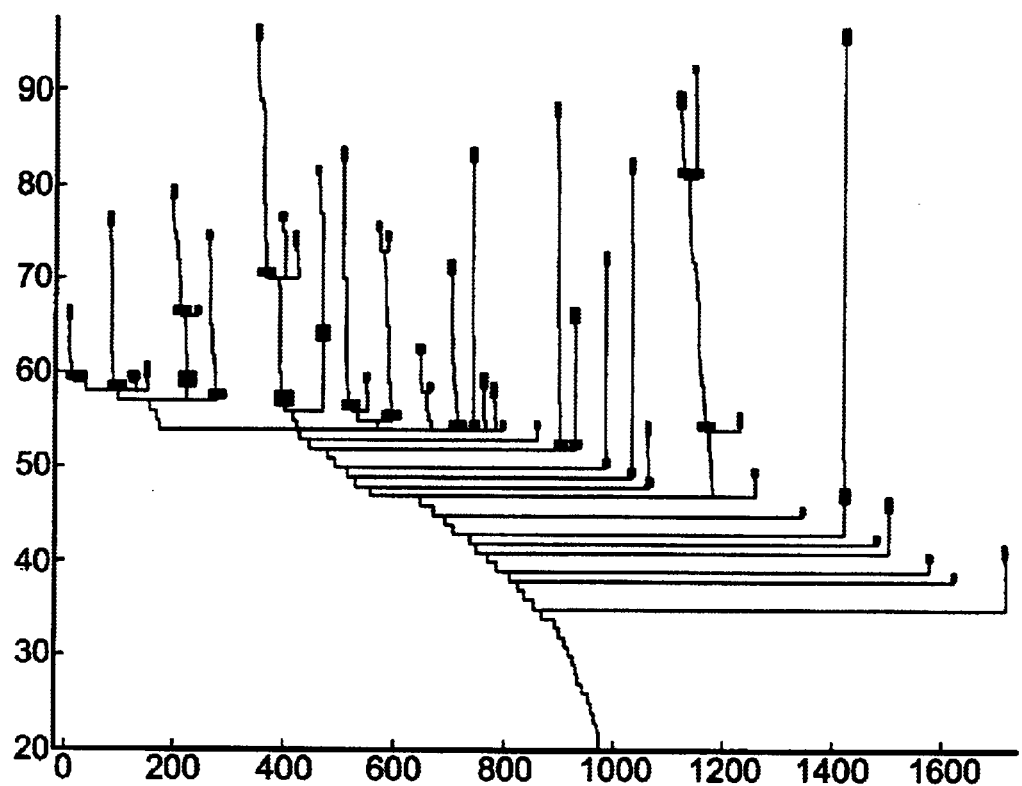
FIG. 2 shows a dendrogram of genes in colon experiment, based on all samples.

The present invention is of a method for coupled two-way clustering, which is able to identify subsets of objects when characterized by a set of features, such that stable and significant partitions emerge. The method of the present invention preferably uses iterative clustering in order to execute this search in an efficient way. Optionally, both the features can be used to cluster the objects and vice versa, for a complete examination of the effect of coupling these two parameters on the emergence of stable clusters and partitions.

For example, according to the method of the present invention, a first plurality of items, such as genes, can optionally be used to partition a second plurality of items, such as the samples for being analyzed according to a characteristic of the genes, and vice versa. For example, the samples can be analyzed in order to determine the expression level of a particular gene or genes, such that the expression level would be an example of a characteristic of the genes. This ability to partition each of two separate groups of items according to the other group can be described as the "two-way" aspect of the method of the present invention. However, the "coupled" aspect of the method of the present invention particularly differentiates the present method from other background art methods. This "coupled" aspect can be generally described as follows: first, discover a subgroup of the first plurality of items, such as a subgroup of genes. Of course any other subgroup of a plurality of items which are linked according to some relationship through the data could be used. Second, use this subgroup of genes to partition the samples, or more generally, use, one at a time, every subgroup of the first group of items to partition the second group of items, and any of its subgroups that have been already identified. The advantage of the "coupled" aspect of the method of the present invention is that the present invention can uncover interactions/partitions which would otherwise be lost in the noise of the overall data.

The coupled two-way clustering method of the present invention is a general way to analyze gene microarray data, and may optionally be used with any suitable clustering algorithm, such that the present invention is not limited to any particular clustering algorithm. A particularly preferred clustering algorithm, which is used in the examples described in greater detail below, is the super-paramagnetic clustering algorithm (SPC) [9, 10, 11, 12]. This algorithm is especially suitable for gene microarray data analysis due to its robustness against noise and its "natural" ability to identify stable clusters.

This algorithm is described in greater detail in U.S. Pat. No. 6,021,383, filed on Oct. 7, 1996 and which is hereby incorporated by reference as if fully set forth herein. U.S. Pat. No. 6,021,383 discloses a method and apparatus for partitioning a data set for clustering, which is based on the physical properties of an inhomogeneous ferromagnet. No assumption needs to be made regarding the underlying distribution of the data. A Potts spin is assigned to each data point and an interaction between neighboring points is introduced, whose strength is a decreasing function of the distance between the neighbors. This magnetic system exhibits three phases. At very low temperatures it is completely ordered, i.e. all spins are aligned. At very high temperatures the system does not exhibit any ordering and in an intermediate regime clusters of relatively strongly coupled spins become ordered, whereas different clusters remain uncorrelated. This intermediate phase is identified by a jump in the order parameters. The spin—spin correlation function is used to partition the spins and the corresponding data points into clusters.

According to preferred embodiments of the present invention, both the number of the features which are used to cluster the data and the number of resultant clustered data points are preferably reduced during the iterative clustering process, such that the data points that are clustered also constitute a subset of the total number available. This approach is particularly preferred for sets of data in which ultimately relatively few data points-may be important. For example, only a small subset of the genes may participate in any given cellular process of interest, such that the large majority of genes act as a source of noise that may mask the correlated activity of the small subgroup of interest. Furthermore, for these types of sets of data, the process of interest is expected to take place only in a subset of the samples; again, by focusing on a small subset, the amount of noise induced by the other samples may be reduced, thereby amplifying the "signal". Hence, the two-way coupled clustering analysis is expected to ultimately locate a relatively small subset F of features (either genes or samples) in order to reveal the structure of a subset O of objects (either samples or genes). The advantages of this approach are demonstrated in greater detail below.

The examples described in greater detail below show the efficacy of the coupled two-way clustering algorithm of the present invention, as implemented with the super-paramagnetic clustering algorithm (SPC), which is known in the art [9, 10, 11, 12]. The coupled two-way clustering method of the present invention was applied to two gene microarray data sets, one from a colon cancer experiment [3] and the other from a leukemia experiment [5]. Also as described in greater detail below, the method of the present invention was able to identify an alternative differentiation between tissues (rather than the expected normal/tumor classification) in the colon cancer experiment, which was then shown to correspond to a change of experimental protocol. In addition, the analysis also revealed evidence for the central role played by epithelial cells in the process of tumor development. In the leukemia experiment, T-cell related genes were shown to be suitable for separating B-cell versus T-cell types of ALL (acute lymphoblastic leukemia)-leukemia. Furthermore, groups of genes were identified whose expression profile differentiates between AML leukemia patients that received treatment and those patients who did not receive such treatment.

The next sections describe the basic method of the present invention for coupled two-way clustering (Section 1); suitable clustering algorithms and similarity measures for use with the method of the present invention (Section 2); various applications of the method of the present invention (Section 3); and various conclusions from the example applications (Section 4). It should emphasized that although the method of the present invention is described with regard to the analysis of gene microarray data, this is for the purposes of discussion only and is without any intention of being limiting. In particular, Sections 3 and 4 provide additional illustrative non-limiting examples of other types of data to which the method of the present invention may also be applied.

Section 1. Coupled Two Way Clustering

Section 1 describes the basic coupled two-way clustering method of the present invention, including a detailed description of each step of the method. In addition, a basic description of the utility of applying the method of the present invention to the analysis of gene microarray data is also provided, although again it should be understood that this is for the purposes of description only and is without any intention of being limiting.

With regard to the basic exemplary algorithm itself, the results of every gene microarray experiment can be summarized as a set of numbers, which are organized in an expression level matrix A. A row of this matrix corresponds to a single gene, while each column represents a given sample. The entry $A_{ij}$ is the normalized expression level of gene i in sample j. The preferred normalization method is described in greater detail below with regard to Section 2, "Clustering method and similarity measures".

In a typical experiment, simultaneous expression levels of thousands of genes are considered. Gene expression is influenced by the cell type, cell-phase, external signals and more [13]. The expression level matrix is therefore the result of all these processes mixed together. The goal is to separate and identify these processes, and to extract as much information as possible about them. The main point is that the biological process of interest may involve a relatively small subset of the genes that are present on a microarray; the large majority of the genes constitute a noisy background which may mask the effect of the small subset. The same result may occur with respect to samples.

The aim of the coupled two-way clustering is to overcome such problems. The method of the present invention attempts to identify subsets of genes $G_\mu$ (to be used as the feature set F) and a subset of samples $S_\alpha$ (which play the role of the set of objects O), such that when the samples are clustered on the basis of their expression profiles over the genes $G_\mu$, a stable and statistically significant partition of $S_a$ is obtained. Alternatively, genes may be selected to play the role of O and samples to serve as F, that yield a partition of the genes of $G_\mu$ into stable meaningful clusters, on the basis of their expression profiles over the samples $S_a$.

The method is illustrated and its advantages are highlighted in an example, based on artificial data, presented in Appendix A.

Clearly the number of ways for choosing sets of genes and samples is exponentially large and one needs an efficient way to search for groups that have the desired property. The method of coupled two-way clustering executes such a search in the following iterative manner. If no information on the data is available and/or should not be used, the process starts with the full data set, and the samples and the genes are then clustered [3]. Next a cluster of genes is chosen, and using these genes as the feature set F to represent the samples, the samples are clustered. The object set O can contain either all the samples or any subset (of sample clusters). Similarly, a cluster of the samples can be chosen and then used as the feature set F to identify stable clusters of genes (which play the role of the objects). All of the stable clusters that are generated, of both genes and samples, are preferably stored, and denoted as $v^g$ (gene cluster), while the samples are denoted as $v^s$. The gene clusters are accumulated in a list $V^g$ and the sample clusters in $V^s$. Furthermore, all of the information about the clustering process that generated every cluster, such as a gene cluster $v^g$, is preferably also stored. More preferably, this information is stored by storing pointers that indicate which sample clusters were used as the feature set; which was the set of genes O that was clustered; as well as pointers to the clusters which were generated when the genes of $v^g$ were used as feature set F to cluster samples.

When new clusters are found, they are used in the next iteration. At each iteration step, a subset of the objects (either samples or genes) is clustered by using a subset of the features (genes or samples). The procedure optionally and preferably only stops when no new relevant information is generated.

The outcome of the coupled two-way clustering algorithm are the final sets $V^g$ and $V^s$, and the pointers that identify how all stable clusters of genes and samples were generated.

The precise step by step definition of an exemplary two-way coupled clustering method according to the present invention is given in FIG. 1. Standard notation is used to describe the method. For example, if U is a subset of V, U\V denotes the complement of U, i.e. all elements of V that are not members of U. The input of the coupled two-way clustering method for the present invention is an expression level matrix A. From this matrix, sets of data points are generated and a pairwise similarity measure is calculated between these sets of data points. The coupled two-way clustering utilizes a clustering algorithm that can identify statistically significant clusters in such a data set. The choice of clustering algorithm, the similarity measure it utilizes, and the manner in which robust, stable clusters are chosen is discussed in greater detail below (Section 2). Even though the choice of the particular clustering algorithm affects the performance of the coupled two-way clustering, the method is applicable for any reasonable choice of such an algorithm.

More specifically, the method of FIG. 1 is preferably performed as follows. In the first stage, initialization is performed. Let $v^g_0$ be the cluster of all genes, and $v^s_0$ be the cluster of all samples. Initialize sets of gene clusters, $V^g$, and sample-clusters, $V^s$, such that $$V^g = \{v^G_0\}$$

and $$V^s = \{v^s_0\}$$

Add each known class of genes as a member of $V^g$, and each known class of samples as a member of $V^s$. Next, define a new set $W=\emptyset$. This set is needed to keep track of clustering analyses that have already been performed.

Next, for each pair:

$$(v^s, v^g) \in (V^g \times V^s) \setminus W$$

the following steps are performed in the second stage.

First, apply the clustering algorithm on the, genes of $v^g$ using the samples of $v^s$ as its features and vice versa. Add all the robust gene clusters generated by the application of clustering algorithm to $V^g$, and all the robust sample clusters to $V^s$. Next, add $(v^g, v^s)$ to W.

In the third stage, for each new robust cluster u in either $V^g$ or $V^s$, define and store a pair of labels $P_u=(u_o, u_f)$. Of these, $u_o$ is the cluster of objects which were clustered to find u, and $u_f$ is the cluster of features used in that clustering.

In the fourth stage, the second stage is preferably repeated until no new clusters are added to either $V^g$ or $V^s$.

After the above method has been performed, the clusters obtained by coupled two-way clustering can be analyzed. The output of coupled two-way clustering has two important features. First, it provides a broad list of gene and sample clusters. Second, for each cluster (of samples, say), the subset (of samples) which was clustered to find that subset is known, and the clusters of the second type, such as of genes, which were used as features are also known. Similarly, the identity of those clusters, which can be found by using it as the feature set for clustering, are also known. The present description concerns a brief, non-limiting selection of examples of the possible uses for this kind of information. Implementations of the particular uses listed here are described in Section 3 below.

First, this information can optionally be used to identify genes that partition the samples according to a known classification. This particular application is supervised. Denote by C a known classification of the samples, say into two classes, $c_1$, $c_2$. The coupled two-way clustering method of the present invention provides an easy way to rank the clusters of genes in $V^g$ by their ability to separate the samples according to C. It should be noted that coupled two-way clustering not only provides a list of candidate gene clusters to be further examined, but also a unique method of testing these candidates.

First, for each cluster of samples $v^s$ in $V^s$, two scores are evaluated, for purity and efficiency, which reflect the extent to which assignment of the samples to $v^s$ corresponds to the classification C. These figures of merit are defined (for both $c_1$, $c_2$) as purity(S|C)=

$$\frac{|v^s \cap c_i|}{v^s}$$

efficiency $(v^s|C)$=

Once a cluster $v^s$ with high purity/efficiency has been found, each of the cluster (or $$\frac{|v^s \cap c_i|}{c_i}$$

clusters) of genes that were used as the feature set can be read to yield $v^s$ in the clustering procedure. Clustering, as opposed to classification, discovers only those partitions of the data which are, in some sense, "natural". Hence by this method, the most natural group of genes that can be used to induce a desired classification is identified.

Needless to say, a gene cluster $v^g$ that was obtained from the coupled two-way clustering method of the present invention can also be tested by using more standard statistics, such as the t-test [14] or the Jensen-Shannon distance [15, 16]. Both compare the expression levels of the genes of $v^g$ on the two groups of samples, $c_1$, $c_2$, which are partitioned according to C. Alternatively, the genes of $v^g$ can optionally be used to train a classifier to separate the samples according to C [5], after which the success of the classifier at measuring whether the expression levels of the genes in $v^g$ correspond to the classification can then be determined.

New partitions of the data can then be discovered. For example, every cluster $v^s$ of $V^s$ contains a subset of all the samples for which the members have been linked to each other, and separated from the other samples on the basis of the expression levels of some feature; with regard to the current example, this feature is the co-expressed subset of genes. It is reasonable therefore to argue that the cluster $v^s$ has been formed for some biological or experimental reason.

As a first step to understand the reason for the formation of a robust cluster $v^s$, the cluster should preferably be related to some previously known classification (for example, in terms of purity and efficiency). Clusters which cannot be associated with any known classification should preferably be inspected more carefully. In the case of the present example, useful hints for the meaning of such a cluster of samples may come from the identity of the cluster of genes which was used to find it. Clearly, the coupled two-way clustering clusters can be used in the same way to interpret clusters of genes which were not previously known to belong to the same process.

Coupled two-way clustering is also a sensitive tool to identify sub-partitions within the data. For example, some of the sample clusters in $V^s$ may have emerged from clustering a subset of the samples, such as $v^s_0$. These clusters reflect a sub-partition of the samples which belong to $v^s_0$. When trying to cluster the full sample set, this sub-partition may be missed, since other samples, unrelated to this subset, are masking it.

Sometimes this procedure reveals that a subgroup $v^s_1$ of $v^s_0$ constitutes a stable sub-cluster, whereas the other samples of $v^s_0$, such as $v^s_0 \backslash v^s_1$, do not form a stable cluster. Nevertheless, the fact that $v^s_1$ is a robust cluster raises the possibility that a relevant sub-partition of $v^s_0$ does exist, which should be investigated.

Furthermore, the coupled two-way clustering method of the present invention can also reveal a conditional correlation among genes. The coupled two-way clustering method collects stable gene clusters in $V^g$. In many cases the same groups of genes may be added to $V^g$ more than once. This is caused by the fact that some genes are co-regulated in all cells, and therefore are clustered together, no matter which subset of the samples is used as the feature set. For example, ribosomal proteins are expected to be clustered together for any set of samples which is not unreasonably small.

Some gene clusters, however, are different, as they are co-regulated only in a specific subset of samples, which can be termed "conditional correlation". The identity of the sample cluster which reveals the conditionally correlated gene cluster is clearly important to understand the biological process which makes these genes correlated.

Section 2. Clustering Method and Similarity Measures

Section 2 describes various similarity measures which can optionally be used with the coupled two-way clustering method of the present invention. As previously described, any suitable similarity measure can optionally be used, although certain similarity measures may be preferred for certain types of data sets, as described in greater detail below with regard to gene microarray data, for example.

As mentioned above, any reasonable choice of clustering method and definition of stable clusters can be used within the framework of coupled two-way clustering. This section describes the particularly preferred clustering algorithm and similarity measure which was used for this particular example of the operation of the present invention, since they were found to be particularly suitable to handle the special properties of gene microarray data.

The super-paramagnetic clustering (SPC) algorithm is a hierarchical clustering method recently introduced by Blatt et al [17], which was found to be particularly robust for the operation of the present invention. Full details of the algorithm [18] and the underlying philosophy [10] are given elsewhere; only a brief description is provided herein, which does not require acquaintance with any concept borrowed from physics.

The input required for SPC is a distance or similarity matrix $d_{ij}$ between the N data points that are to be clustered. From such a distance matrix, a graph is constructed, whose vertices are the data points, and whose edges identify neighboring points. Two points i and j are called neighbors (and connected by an edge) if they satisfy the K-mutual-neighbor criterion, i.e. if and only if j is one of the K nearest points to i and vice versa. A weight $J_{ij}>0$ is associated with each edge, which decreases as the distance between points i and j increases.

Every possible assignment of the data points to clusters is equivalent to a partition S of this weighted graph, with the connected components of the partitioned graph playing the role of clusters. Every partition S is characterized by its cost H[S], which is the sum of the weights $_{ij}$ of all the edges that were cut in order to create the corresponding partition of the weighted graph.

There is an exponential number of possible partitions which can be generated. These range from partitions with all points assigned to the same single cluster, which has the lowest possible cost H=0, to partitions corresponding to the maximal H, obtained when all edges are cut and each point constitutes its own individual cluster. By fixing the value of H, control is provided over the resolution at which the data is to be clustered.

However, even if the cost is constrained to lie within a certain interval $E<H<E+\Delta$, there may be a very large number of partitions that satisfy this constraint. Rather than selecting a particular partition, preferably an ensemble of partitions is created, assigning equal statistical weight to every partition of the graph whose cost lies in the prescribed interval, optionally and more preferably using the maximum entropy principle. Next, the probability $p_{ij}$, that in this ensemble of partitions the vertices i and j belong to the same cluster, is preferably measured for every pair of neighboring points i, j; $p_{ij}$ is called the pair correlation function, which is used to identify the clusters that constitute the output of the algorithm, such that a high correlation means that at the working resolution E, the two data points belong to the same cluster. That is, a new graph is generated by connecting two points ij by an edge, provided $p_{ij} > \frac{1}{2}$. Optionally, a slightly more complicated procedure is used to generate this graph from $p_{ij}$, as is described in the background art [18]. This procedure is optionally and more preferably performed at a sequence of resolutions. As the resolution parameter E is increased from its lowest value, a dendrogram of nested partitions, or clusters, is generated.

This simple explanation of the algorithm needs to be supplemented by one caveat; rather than generating an ensemble of equally likely partitions at a fixed E, the procedure operates at a fixed average cost, tuned by a Lagrange multiplier which can be denoted by 1/T. The ensemble is then preferably generated by a Monte Carlo sampling procedure [19].

The procedure outlined above may be considered to be analogous to the simulation of a Potts ferromagnet at thermal equilibrium, where the weights $J_{ij}$ are the couplings between neighboring spins, T is the temperature and $p_{ij}$ is the spin-spin correlation function. At T=0 the system is in its (fully aligned) ground state, all neighbor pairs have correlations $p_{ij}=1$ and a single cluster is obtained. As the resolution T increases, phase transitions occur, with the single ferromagnetic domain breaking up into sub-clusters. These transitions can be very sharp, in which case the corresponding splits can be easily identified. Clusters continue to decompose as the system is "heated" further, until at a sufficiently high "temperature", each point forms its own cluster (see FIG. 2 for an illustration of this process).

Blatt et al showed that the SPC algorithm is robust against variation of its parameters, initialization and against noise in the data [18]. Due to these distinct advantages, the SPC algorithm is especially suitable for gene microarray data analysis. No prior knowledge of the structure of the data is assumed. The SPC algorithm provides information about the different self-organizing regimes of the data; the number of "macroscopic" clusters is an output of the algorithm; hierarchical organization of the data is reflected in the manner clusters merge or split when the control parameter (the "temperature" T) is varied.

The SPC algorithm has the further advantage of providing clear identification of stable clusters. The clusters generated by SPC are governed by the value of a continuous control parameter T, which controls the resolution at which clustering is performed. This parameter can be used to provide a natural measure for the stability of any particular cluster by the range of temperatures $\Delta T$ at which the cluster remains unchanged. A stable cluster is expected to 'survive' throughout a large $\Delta T$, one which constitutes a significant fraction of the range it takes the data to break into single point clusters. Inspection of the gene dendrogram of FIG. 2 reveals stable clusters and stable branches.

Each node of the dendrogram of FIG. 2 represents a cluster; only clusters of size larger than eight genes are shown. The last such clusters of each branch, as well as non-terminal clusters that were selected for presentation and analysis are shown as boxes. The circled boxes represent the clusters that are discussed below. Proximity of two clusters along the horizontal axis indicates that the corresponding temporal expression profiles are not very different [3]. The vertical axis represents the resolution, controlled by the "temperature" T. The vertical position of a node or box is determined by the value of T at which it splits. A high vertical position indicates that the cluster is stable, i.e. contains a fair number of closely spaced data points (genes with similar expression profiles).

The gene expression array can also optionally be normalized for the operation of the method of the present invention, as described with regard to the following example. The Pearson correlation is commonly used as the similarity measure between genes or samples [20, 4, 3]. This measure conforms with the intuitive biological notion of what it means for two genes to be co-expressed; this statistic captures similarity of the "shapes" of two expression profiles, and ignores differences between the magnitudes of the two series of measurements [4]. The correlation coefficient is high between two genes that are affected by the same process, even if each has a different gain due to the process, over different background expression levels (caused by other processes). One problem of using the correlation coefficient is that its reliability depends on the absolute expression level of the compared genes, since a positive correlation between two highly expressed genes is much more significant than the same value between two poorly expressed genes. This information is ignored in the clustering process.

However, correlations do not always capture similarity between samples. For example, consider two samples taken at different stages of some process, with the expression levels of a family of genes much below average in one sample and much higher in the other. Even if the expression levels of the two samples over these genes are correlated, preferably they are assigned into different clusters. Furthermore, the distance between the two samples should be affected by the statistical significance of their expression differences. This can be obtained if the Euclidean distance between normalized gene expressions is used as the distance measure between samples.

Therefore the following normalization scheme was used for this example. Denote by D the matrix of the raw data. Each row of this matrix represents a single gene, while each column represents a sample. The entry $D_{ij}$ is the measured expression level of gene i in sample j. D is a $n_g \times n_1$ matrix, where $n_g$ is the number of genes and $n_1$ is the number of samples.

The expression level matrix is then preferably normalized in two steps. First, divide each column by its mean:

$$D'_{ij} = D_{ij}/\overline{D}_{ij}$$

and $$\overline{D}_j = \frac{1}{n_g} \sum_{i=1}^{n_g} D_{ij}$$

Each row is then normalized, such that its mean vanishes, and the norm is one:

$$A_{ij} = \frac{D'_{ij} - \overline{D}'_i}{\|D'_i\|}$$

where $$\overline{D}'_i = \frac{1}{n_i} \sum_{j=1}^{n_i} D'_{ij}$$

and $$\|D'_i\|^2 = \Sigma_{j=1}^{n_i} (D'_{ij} - \overline{D}'_i)^2$$

For genes and samples, the Euclidean distance is used as the dissimilarity measure. For two genes (rows of A), the Euclidean distance is closely related to the Pearson correlation between them. For two samples, the Euclidean distance between their respective columns provides the dissimilarity measure.

Section 3. Applications

Section 3 describes various applications of the method of the present invention for coupled two-way clustering through a number of examples. It should be noted that these examples are intended only for illustrative purposes and are without any intention of being limiting. The coupled two-way clustering method of the present invention is therefore applied to two gene microarray experiment data sets. In this particular section, only the results which were obtained by coupled two-way clustering and which could not be found using a straightforward clustering analysis are described. Full lists of several clusters mentioned in this section can be found in Appendix B.

The first example concerns the analysis of leukemia samples. Data available at [21], obtained by Golub et al [5] from seventy-two samples collected from acute leukemia patients at the time of diagnosis, was analyzed. Forty-seven cases were diagnosed as ALL (acute lymphoblastic leukemia) and the other twenty-five were diagnosed as AML (acute myeloid leukemia). RNA prepared from the bone marrow mononuclear cells was hybridized to high-density oligonucleotide microarrays, produced by Affymetrix (3380 Central Exway, Santa Clara, Calif. 95051, USA), containing 6817 human genes.

After rescaling the data in the manner described by Golub et al, only those genes whose minimal expression over all samples is greater than twenty were selected. As a result of this thresholding operation , 1753 genes remained. The resulting array was then normalized as described in Section 2, to give the 1753×72 expression level matrix A.

Figure 3:
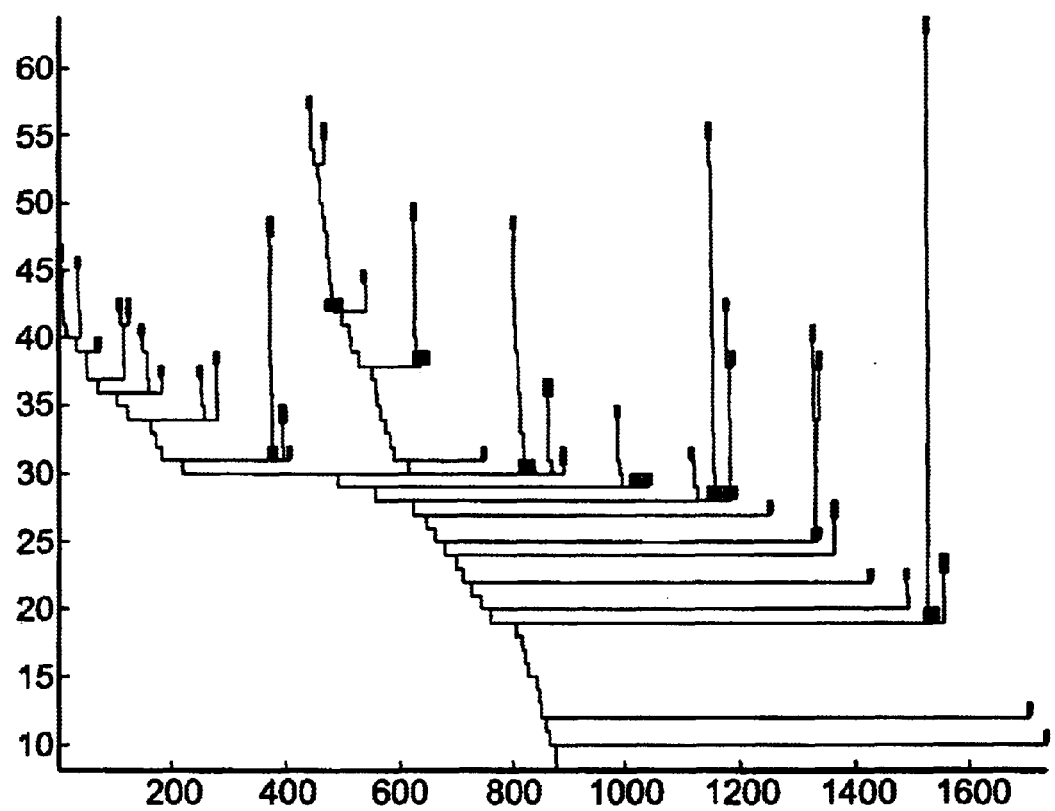
FIG. 3 shows a dendrogram of genes in leukemia experiment, based on all samples.
Figure 5:
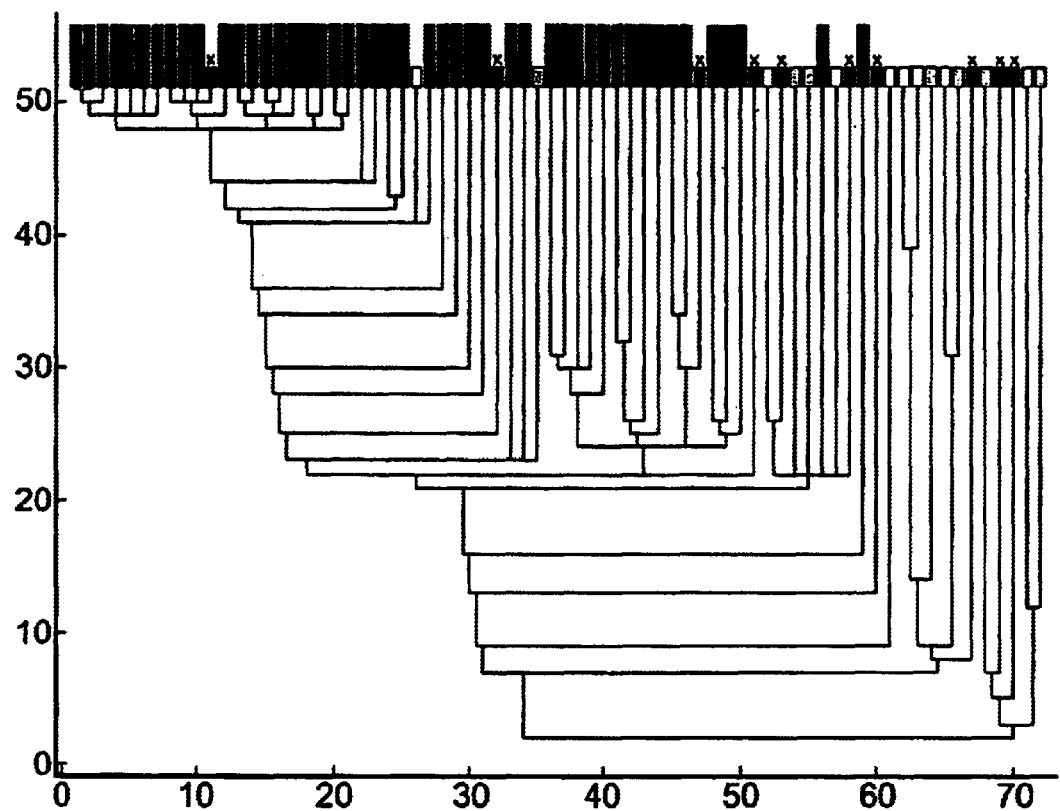
FIG. 5 shows a dendrogram of all samples in the leukemia experiment, based on the genes of cluster LG1. Code as for FIG. 4.
Figure 6:
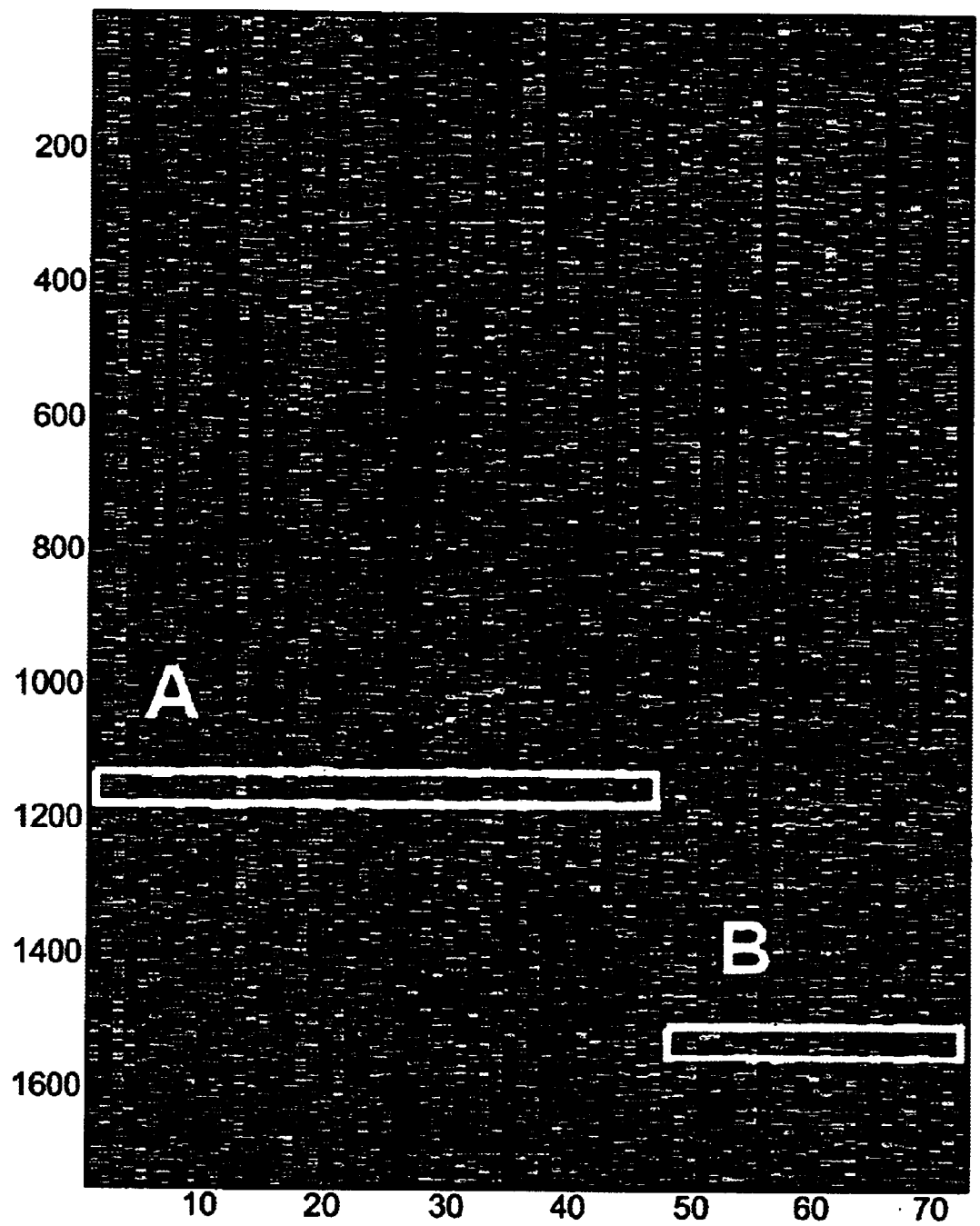
FIG. 6 shows an expression level matrix of the leukemia experiment. Rows, corresponding to genes, are ordered according to the gene clusters of FIG. 3. The two boxes contain expression data from ALL patients (A) measured on one gene cluster and AML patients (B), on another gene cluster.
Figure 7:
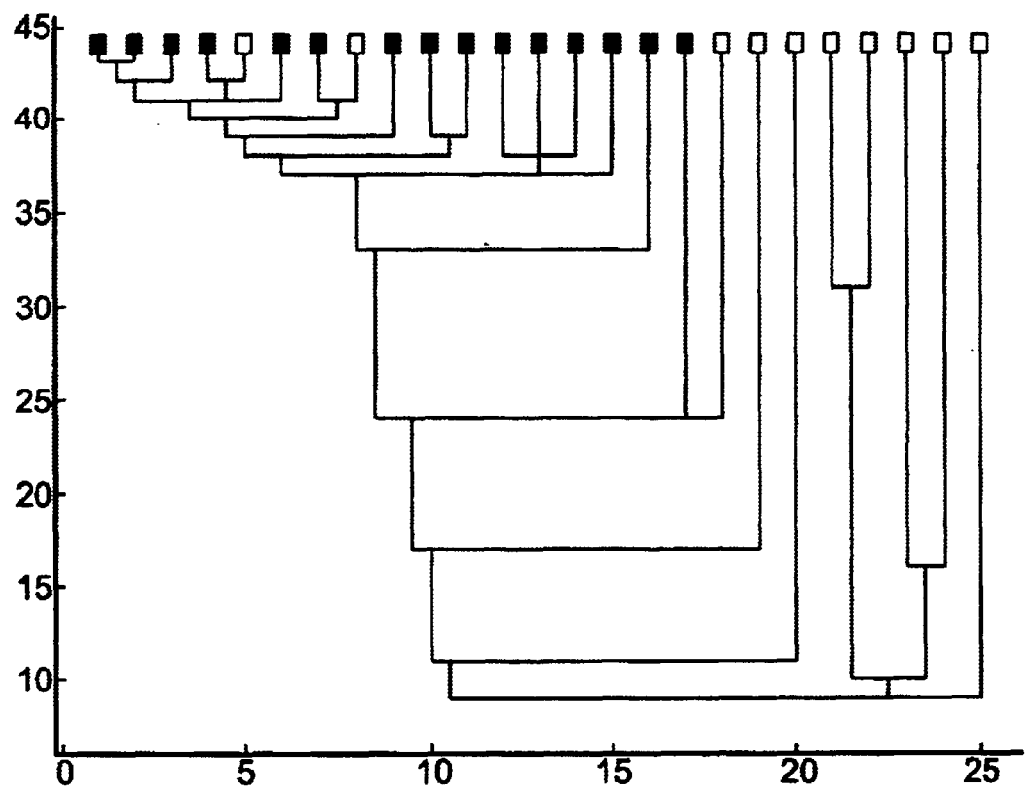
FIG. 7 shows the results of clustering AML leukemia samples, based on genes of cluster LG4. Patients whose treatment succeeded (black) or failed (gray) are clustered into a stable cluster.

First, these genes were clustered by using all samples as the feature set. The resulting dendrogram of genes is shown in FIG. 3. Next, all samples were clustered by using all of the genes as the feature set. The resulting dendrogram of samples is given in FIG. 7. The various gene clusters of FIG. 3 were then used, one at a time, to cluster all the samples. The dendrogram obtained using only the gene cluster LG1 (see below) is shown in FIG. 5. The rows of the expression matrix were permuted according to the ordering [3 ] of the gene clusters of FIG. 3. A color-coded permuted expression level matrix is shown in FIG. 6.

Two iterations of the coupled two-way clustering algorithm, as previously described in Section 1, were found to be sufficient to converge to forty-nine stable gene clusters (LG1–49) and thirty-five stable sample clusters (LS1–35). In particular, four results from these findings are described in greater detail below in order to demonstrate the power of the method of the present invention to solve problems listed in Section 1.

The first such result is the ability of the method of the present invention to identify genes that partition the samples according to a known classification. Since the ALL/AML classification of the patients is known in advance, the present invention can be used to search for groups of genes that distinguish between the two classes. To test a given gene cluster the mean expression of all of its genes is calculated for every patient. Next, the forty-five values derived for the ALL patients are postulated to have been drawn from one probability distribution and the values of the AML patients are postulated to have been drawn from another probability distribution. The t-test statistic for these distributions was then evaluated, and five gene clusters were found with an exceptionally high t-test score. This means that the genes from these five clusters have very different expression levels for ALL and AML patients.

An alternative approach to this question is to examine whether the samples split into two clusters according to the ALL/AML diagnosis, when the expression levels of genes from a single gene cluster are used as the characteristic features. A cluster of samples is then identified as ALL or AML only if both its purity and efficiency exceed 0.75, measured with respect to the known classification.

The data analysis showed that only a single gene cluster (LG1) provided features that produce ALL or AML clusters. This cluster indeed has a high t-test score. For the other high t-test gene clusters, the overlap between the two clouds of sample points, corresponding to ALL and AML, was too high to allow separation into two distinct clusters. If the data points of the two types of samples form a single continuous cloud, the SPC algorithm cannot break them into two clusters even when there exists a clear dividing hypersurface that separates the two types of samples. In such cases the SOM algorithm used by Goloub et al [5] and the WARD agglomerative algorithm [22, 16] may be preferred, for example. Both of these algorithms can break a single large group or cloud of points into two subclouds of (usually) equal volumes, which may then correspond to the correct partition.

Figure 4:
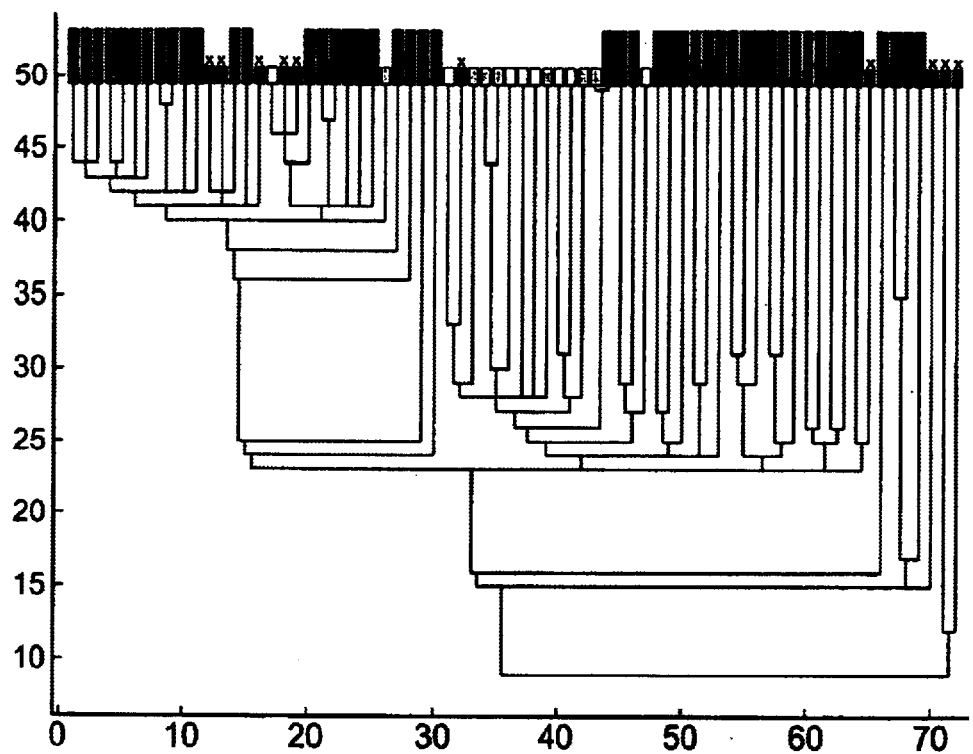
FIG. 4 shows a dendrogram of all samples in the leukemia experiment, based on all genes. High boxes are ALL samples (T-ALL in gray, B-ALL in black). Short boxes are AML samples (coded according to treatment results—white for success, diagonal hatch marks for failure, black with an "x" for unknown).

To demonstrate the power of coupled two-way clustering, it should be noted that when the expression levels of all of the genes are used as the features, the samples do not break into distinct stable ALL and AML clusters, whereas when the single gene cluster LG1 is used, the samples can be broken into distinct stable ALL and AML clusters (see FIGS. 4 and 5).

The present invention is also suitable for discovering new partitions of existing data sets. For example, the stable sample clusters can be optionally searched for unknown partitions of the data. Attention is then preferably focused on sample clusters which were repeatedly found to be stable. One such cluster, denoted LS1, may be of interest; it includes thirty-seven samples and was found to be stable when either a cluster of twenty-seven genes (LG2) or another unrelated cluster of thirty-six genes (LG3) was used to provide the features. LG3 includes many genes that participate in the glycolysis pathway. Due to lack of additional information about the patients, the biological origin of the formation of this sample cluster cannot be further analyzed.

As a further step, the data sets can optionally be analyzed in order to identify subpartitions within the clusters of data points. The samples that were identified as AML patients (leaving out ALL samples) were used as the object set. These samples were then analyzed according to the method of the present invention, in an attempt to cluster these samples by sequentially applying each of the gene clusters as the feature set. Emergent stable subpartitions of the AML patients were then analyzed. Indeed, using a twenty-eight gene cluster (LG4) as the feature set, a stable cluster, LS2, of sixteen samples was found (see FIG. 7). It contains fourteen out of the fifteen samples that were taken from patients that underwent treatment and whose treatment results were known (either success or failure). No information about treatment was available in the data for any of the other AML patients. Some of the sixteen genes of this cluster, (LG4), are ribosomal proteins and others are related to cell growth (see Appendix B). Apparently these genes have different expression patterns for those AML patients who received treatment, as opposed to those patients who did not receive such treatment.

Figure 8:
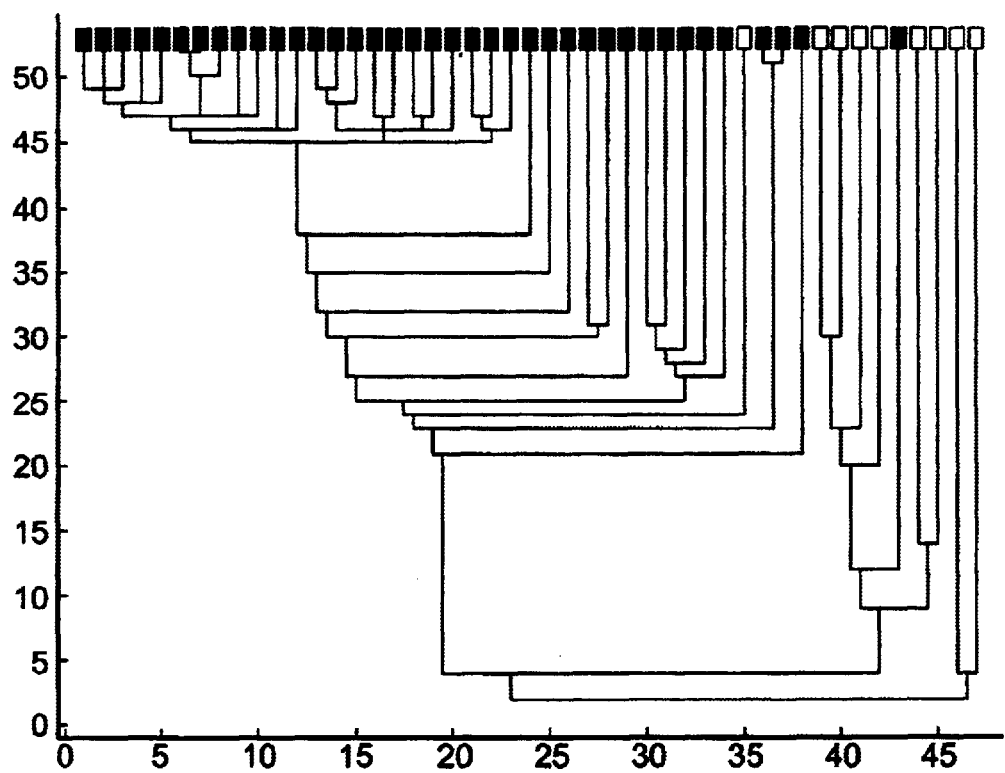
FIG. 8 shows the result of clustering ALL leukemia samples, based on genes of cluster LG5. Good separation between T-ALL (black) and B-ALL (white) is obtained.

The same procedure was then repeated, but discarding AML samples and keeping only the ALL samples. When any one of five different gene clusters (LG4–8) were used to provide the features the ALL samples were found to break into two stable clusters. The first stable cluster consists mostly of T-Cell ALL patients and the second stable cluster contains mostly B-Cell ALL patients. One of these gene clusters, (LG5), with the ability to separate between the T-Cell and B-Cell varieties, contains twenty-nine genes; indeed, many of the genes are T-cell related. Using (LG5) as the feature set, and the ALL samples as the object set, two clear sub-clusters were found; LS3, of seven samples and LS4, of thirty-eight samples (see FIG. 8). The first sub-cluster, LS3, captured six out of the nine patients diagnosed as T-ALL; the second, LS4, contained thirty-seven out of the thirty-eight B-ALL patients. On the other hand, when all of the genes were used to cluster all samples, no such clear separation into T-ALL vs B-ALL was observed.

It should be noted that another gene cluster, LG6, which gave rise to T-ALL/B-ALL differentiation, contains many HLA histocompatability genes.

These results demonstrate how coupled two-way clustering can optionally be used to characterize different types of cancer. For instance, imagine that the nature of the sub-classification of ALL had not been known. On the basis of these results, the existence of two distinct sub-classes of ALL could be predicted; moreover, by the fact that many genes which induce separation into these sub-classes are either T-Cell related or HLA genes, these sub-classes could be suspected to be immunology related.

As a different possible use of these results, note that some of the genes in the T-Cell related gene cluster LG5, have no determined function, and may be candidates for new T-Cell genes. This assumption is supported both by the fact that these genes were found to be correlated with other T-Cell genes, and by the fact that they support the differentiation between T-ALL and B-ALL.

For further analysis of gene clusters, conditional correlations among genes may be considered. Most of the gene clusters are stable against changing the set of samples that are used to provide the features for clustering. This means that most gene clusters contain genes that are highly correlated over any subset of the samples. However, a few gene clusters were found which exhibit conditional correlations. The genes of two groups, LG9 and LG10, are correlated over the ALL samples; they do not form clusters when either in the AML or the full sample set are used. Hence the genes of LG10 probably take part in a biological process which is characteristic of ALL samples. On the other hand, three groups of genes, LG11, LG12 and LG13, were found to form clusters only over the AML sample set.

As a second illustrative example of the operation of the method of the present invention, a set of data for colon cancer was analyzed. This data set contains 40 colon tumor samples and 22 normal colon samples, which were analyzed with an Affymetrix oligonucleotide array complementary to more than 6500 human genes and expressed sequence tags (ESTs) (Affymetrix Hum6000 array; see Alon et al [3] for details). Following Alon et al [3] only the 2000 genes of greatest minimal expression over the samples were considered. The data set is publicly available at [23]. The data were normalized as previously described in Section 2, to obtain a 2000×62 expression level matrix A.

Figure 9:
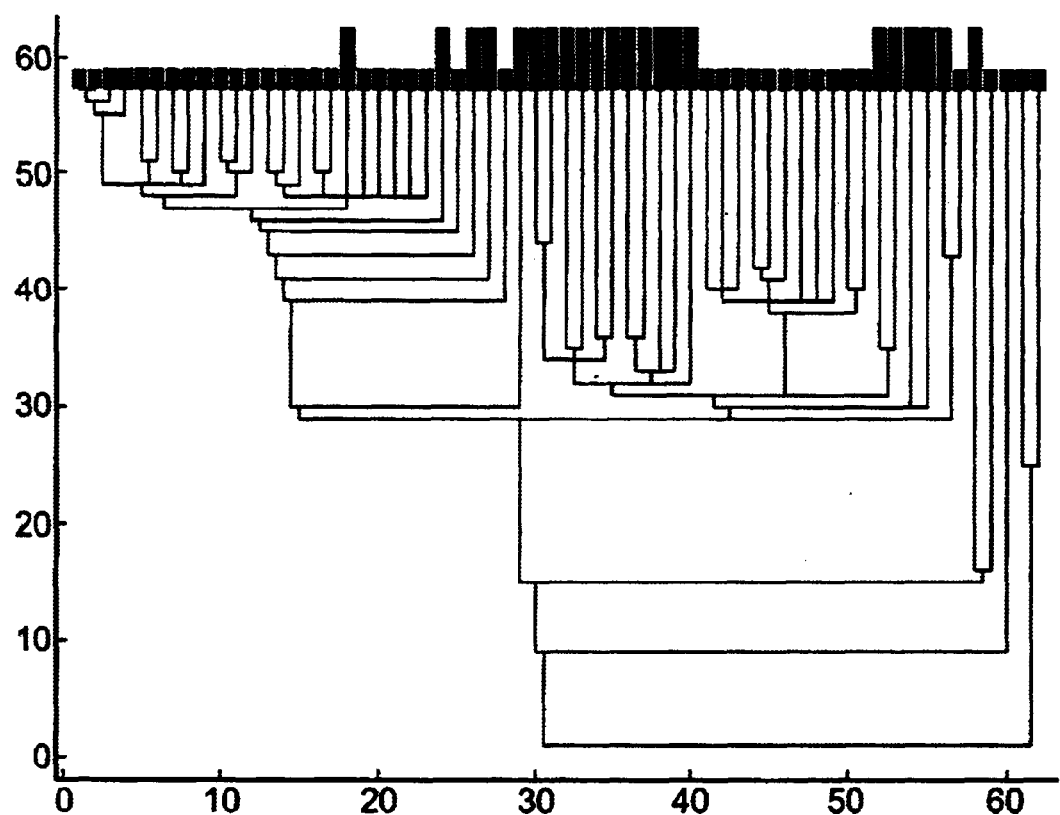
FIG. 9 shows the result of clustering colon samples, based on all genes. Fairly good separation between tumor (white) and normal (black) samples is obtained. The height of the boxes is according to experiment protocol.
Figure 14:
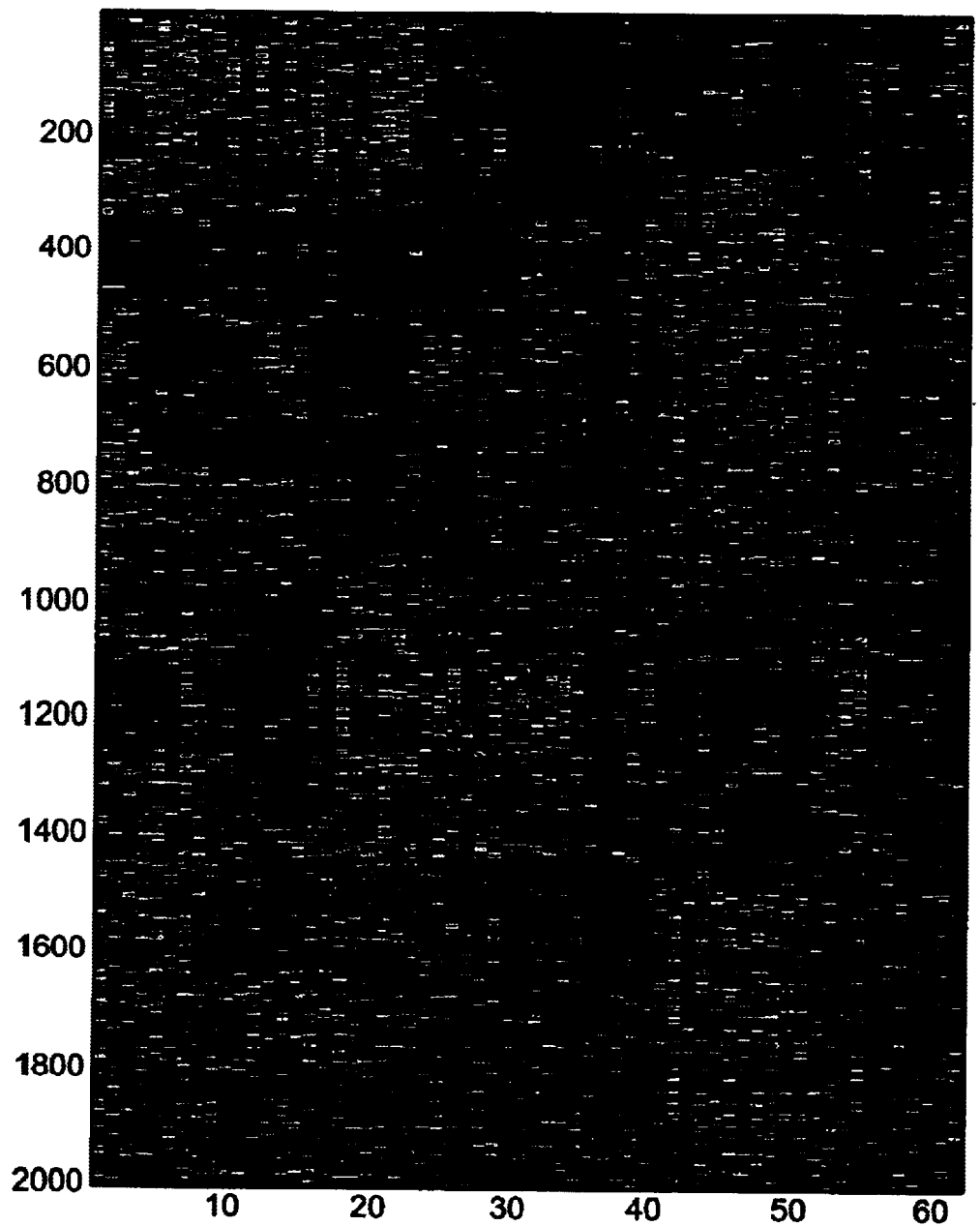
FIG. 14 shows an expression level matrix of the colon experiment. A lighter shade indicates a higher expression level.

First, the genes were clustered, using all tissues as the feature set; the clusters were ordered [3] (see dendrogram of FIG. 2) and the rows of the expression matrix were reordered accordingly. The tissues were clustered using all genes as the feature set (see FIG. 9): the columns of the expression matrix were then reordered. The result is shown in FIG. 14.

The coupled two-way clustering method of the present invention, as described in Section 1, was applied to this data set. Ninety-seven stable gene clusters (CG1–97) and seventy-six stable sample clusters (CS1–76) were obtained in two iterations. Again, results are presented which correspond to the four items of Section 1.

Figure 10:
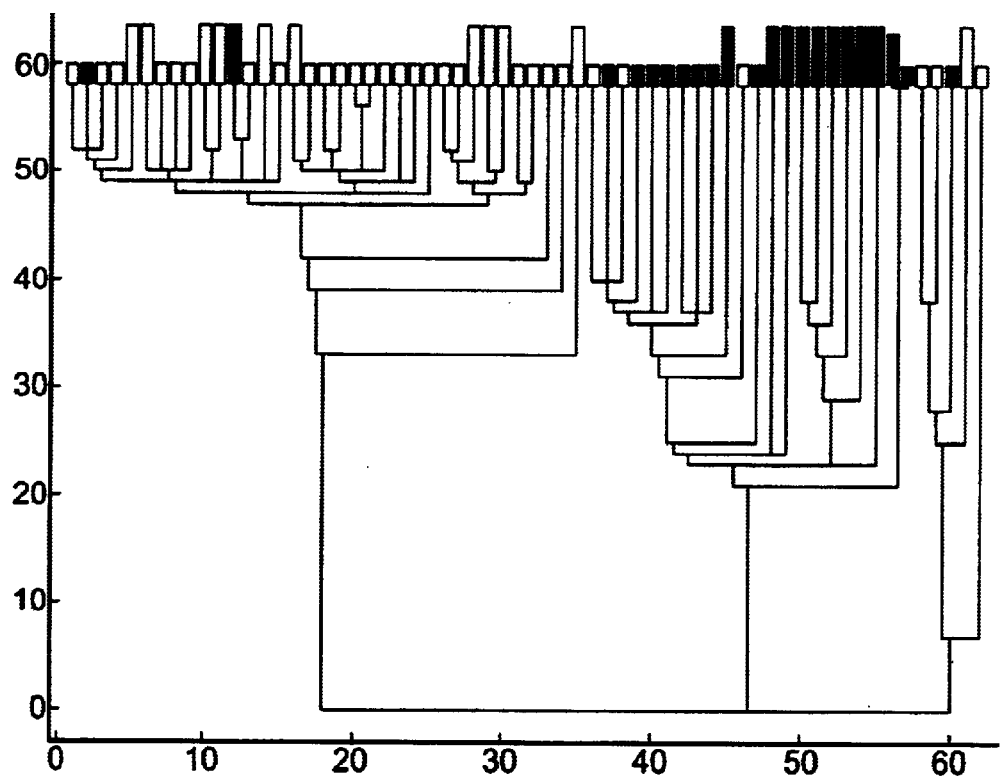
FIG. 10 shows the result of clustering colon samples, based on genes of cluster CG2. Clearer separation between tumor (white) and normal (black) samples is obtained. The height of boxes is according to the experiment protocol.

First, genes were identified that partition the samples according to a known classification. To search for gene clusters which differentiate the samples according to the known normal/tumor classification, the t-test statistic is evaluated for each gene cluster in the manner described above. Six gene clusters with relatively high t-test scores were found. Next, the data is searched for gene clusters which, when used as the features that characterize the samples, give rise to stable normal/tumor clusters (see FIG. 10). Four gene clusters (CG1–4) can be used this way to partition the samples into clusters that contain predominantly normal/tumor tissues (as for the previous data, purity and efficiency above 0.75 were required). Two of these four clusters also have high t-test scores.

Figure 11:
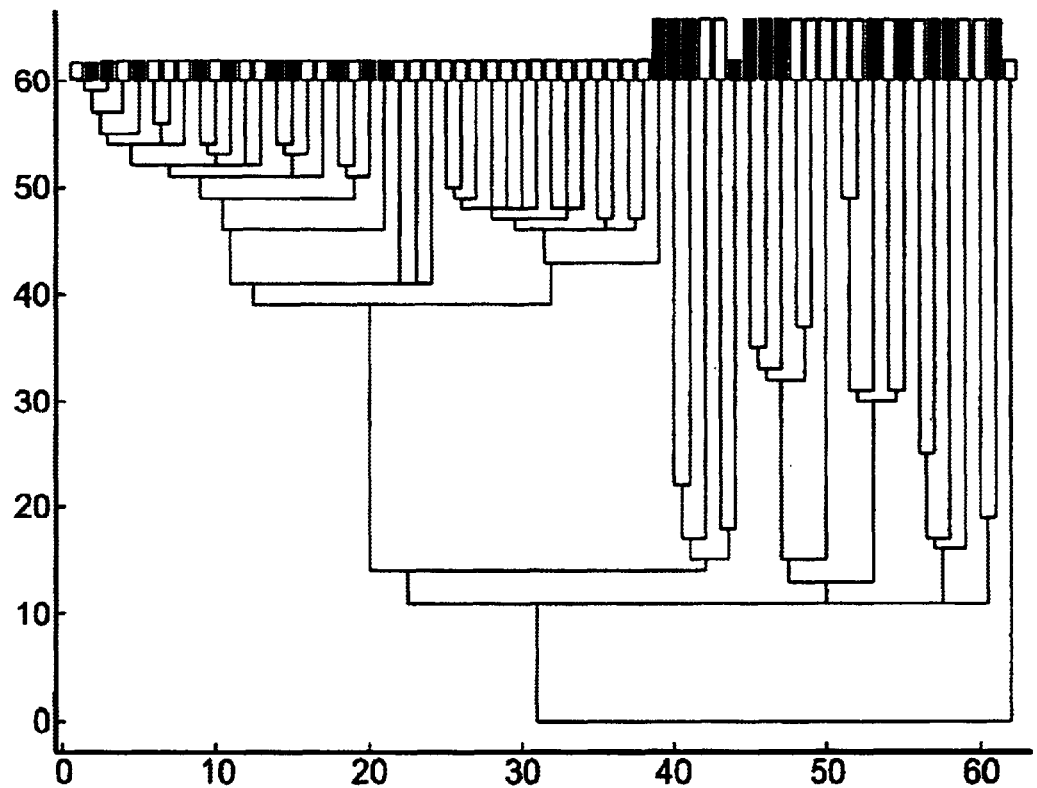
FIG. 11 shows the result of clustering colon samples, based on genes of cluster CG5. Another separation of the samples is obtained using this gene cluster. This separation is consistent with the two experiment protocols, A (short) and B (tall). Colors are according to tumor (white) vs normal (black).

These data can also optionally be further analyzed in order to discover new partitions. The stable sample clusters were further analyzed, searching for unknown partitions of the data. Five clusters of genes (CG2, CG4–7) that generate very stable clusters of samples were found. Two of the five clusters are able to differentiate tumor and normal tissues. Another two clusters are less interesting since they gave rise to stable clusters that contained most of the samples. The gene cluster CG5 gave rise to a clear partition of the samples into two clusters, one containing thirty-nine samples and the second containing the remaining twenty-three samples (see FIG. 11). According to an examination of the experimental protocol from which the original-data were obtained, this separation coincides almost precisely with a change of the experimental protocol which was used: the first 22 RNA samples (eleven normal and eleven tumor) were extracted using a poly-A detector ('protocol-A'), and the other forty samples (eleven normal and twenty-nine tumor) were prepared by extracting all RNA from the cells ('protocol-B'). Thirty-eight out of the thirty-nine samples in the large cluster were taken using protocol-B. No common features were found among the twenty-nine genes of the cluster CG5 that gave rise to the separation according to the two protocols.

Figure 12:
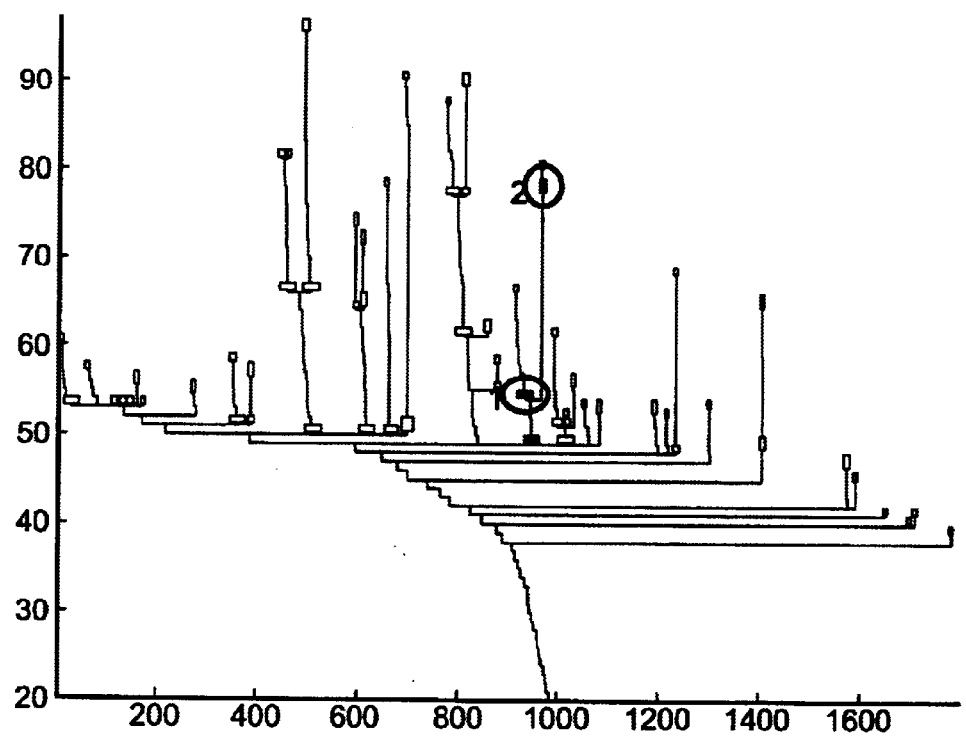
FIG. 12 shows a dendrogram of genes in colon experiment, based only on tumor samples. The marked clusters appear here close to each other and share a common 'parent' in the graph, hence the two are relatively correlated.

As in the case of the leukemia data which were previously described, here again most gene clusters form irrespectively of the samples that are used as features. However, five special groups of genes (CG8–11) were found. When all the samples were used as the feature set to cluster the genes, none of these five groups formed a cluster; similarly, when only the normal samples were used, these genes were relatively uncorrelated, i.e. spread across the dendrogram of genes. On the other hand, when the tumor samples were used as the feature set, each of these five groups formed a clear, stable cluster. The genes of each of these five clusters were used as the object set and clustered, using the tumor samples as the feature set. One of these five clusters, (CG9), was found to disintegrate, at a higher resolution, into two sub-clusters (see FIG. 12).

Figure 13:
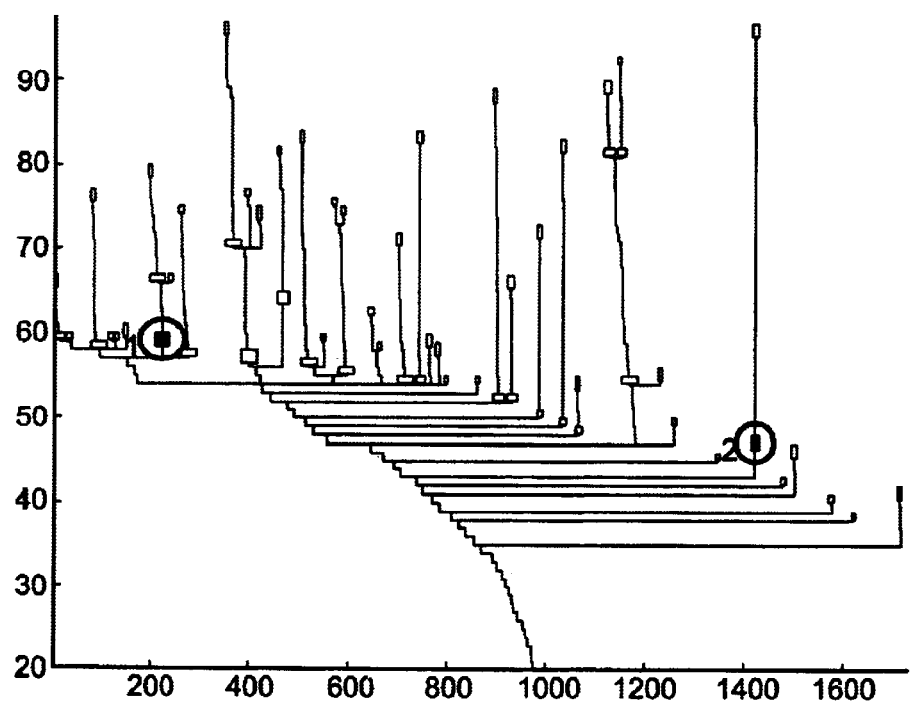
FIG. 13 shows a dendrogram of genes in colon experiment, based on all samples. The marked clusters are those which are marked in FIG. 12, except that here the two are not correlated.

Another one of these sub-clusters, (CG12), consists of fifty-one genes, all of which are related to cell growth (ribosomal proteins and elongation factors). The other sub-cluster, (CG13) contains seventeen genes, many of which are related to intestinal epithelial cells (e.g. mucin, cathespin proteases). Interestingly, when clustering the genes on the basis of the normal samples, both (CG12 and CG13) appear as two distinct clusters, but while these clusters are "daughters" of the single cluster (CG9) over the tumor samples, they are not correlated over the normal samples and their positions in the dendrogram of FIG. 13 are quite far from each other.

The high correlation between growth genes and epithelial genes, observed in the tumor tissue, suggests that it is the epithelial cells that are rapidly growing. In the normal samples there is smaller correlation, indicating that the expression of growth genes is not especially high in the normal epithelial cells. These results are consistent with the epithelial origin of colon tumor.

Two other groups of genes formed clusters only over the tumor cells. One (CG11, containing thirty-four genes) is related to the immune system (HLA genes and immunoglobulin receptors). The second (CG10, containing sixty-two genes) seems to be a concatenation of genes related to epithelial cells (endothelial growth factor and retinoic acid), and of muscle and nerve related genes. No common function for the genes in the fourth cluster (CG8) was found.

Clustering the genes on the basis of their expression over only the normal samples revealed three gene clusters (CG14–16) which did not form when either the entire set of samples or the tumor tissues were used. Again, a clear common function for these genes was not found. Each cluster contains genes that apparently participate in one or more processes which occur in normal cells, but is suppressed or absent in tumor tissues.

Section 4. Summary and Discussion

The preceding sections describe a new method for analysis of large amounts of data, such as gene microarray data. The main concept of the method of the present invention is to locate features of interest within such large sets of data, as for example small subsets of the massive expression patterns obtained from thousands of genes for a large number of samples. A cellular process of interest may involve a relatively small subset of the genes in the data set, and the process may occur only in a small number of samples. Hence when the full data set is analyzed, the "signal" of this process may be completely overwhelmed by the "noise" generated by the vast majority of unrelated data.

The specific examples illustrated in the preceding sections concerned the determination of a relatively small group of genes from a rather large experimental set, which can be used as the features for clustering a subset of the samples. Alternatively, a subset of the samples that can be used in a similar way to identify genes with correlated expression levels can also optionally be identified, as described above. Identifying pairs of subsets of those genes and samples which produce significant stable clusters is a computationally complex task. The coupled two-way clustering method of the present invention provides an efficient mechanism for producing such subgroups.

The basic coupled two-way clustering method of the present invention is simple. For example, with regard to the gene microarray data described above, initially the cluster structure of the full data set is found, both in gene and in sample space. The resulting clusters are then used again, either as new sets of objects to be clustered, or as features, to be used to cluster some limited set of objects. The method of the present invention then provides a broad list of stable gene and sample clusters, together with various connections among them. For example, for every cluster of samples $v^s$, the features (i.e. the gene clusters) that were used to generate each cluster are known. Also, the set of samples on which the clustering was performed is known. This information can be used to perform the most important tasks in microarray data analysis, such as identification of cellular processes and the conditions for their activation; establishing connection between gene groups and biological processes; and finding partitions of known classes of samples into sub-groups.

The coupled two-way clustering method of the present invention has been demonstrated to be computationally feasible for the cases which were studied. One of the reasons is that the stable clusters generated by the procedure become small with increasing iterations. Therefore their clustering analysis gets faster, and the method typically stops after only a few iterations. The method of the present invention is applicable with any reasonable, suitable choice of clustering algorithm, as long as the selected algorithm is capable of identifying stable clusters. The examples of analyses which were described above concerned one exemplary but preferred clustering algorithm, which is super-paramagnetic clustering algorithm (SPC). This algorithm is especially suitable for gene microarray data analysis due to its robustness against noise which is inherent in such experiments.

The power of the coupled two-way clustering method according to the present invention was demonstrated on data obtained in two gene microarray experiments. In the first experiment the gene expression profile in bone marrow and peripheral blood cells of seventy-two leukemia patients was measured using gene microarray technology. The main results for this data analysis can be summarized as follows. First, the connection between T-Cell related genes and the sub-classification of the ALL samples, into T-ALL and B-ALL, was revealed in an unsupervised fashion. Hence coupled two-way clustering can be used to identify genes whose expression profiles are different for different kinds of cancer. Second, a stable partition of the AML patients into two groups was also found. The first group contained those patients who were treated (with known results), and the second group contained all other patients. This partition was revealed by a cluster of cell growth related genes.

The second experiment used gene microarray technology to probe the gene expression profile of forty colon tumor samples and twenty-two normal colon tissues. Partition of the samples of this experiment into clusters of tumor and normal tissues is an easy task [16]. The method of the present invention also detects a different, less obvious stable partition of the samples into two clusters. To find this partition, a subset of the genes was used. The new partition turned out to reflect the existence of two different experimental protocols which were used to generate the data Without wishing to be limited to a single hypothesis, it may be deduced that the genes which gave rise to this partition of the samples are those genes which were sensitive to the change of protocol.

Another result, that was obtained in an unsupervised manner using the method of the present invention, is the connection between epithelial cells and the growth of cancer. When the expression profiles were considered over only the tumor tissues, a cluster of cell growth genes was found to be highly correlated with epithelial genes. This correlation was absent when the normal tissues were used.

These novel features, discovered in data sets which were previously investigated by conventional clustering analysis, demonstrate the strength of the coupled two-way clustering method of the present invention. The coupled two-way clustering method was found to be especially useful for gene microarray data analysis, but it may be a useful tool for investigating other kinds of data as well.

For example, the method of the present invention is also optionally used to classify documents. These documents may be individually characterized according to the number of times each of a plurality of keywords appears in the document. However, simply examining the overall pattern of keyword frequency in the documents may obscure interesting partitions, or associations within the group of documents which may only characterize a subgroup of the documents. Therefore, according to the method of the present invention, the keywords themselves are optionally first examined for possible partitions and/or associations within this group of keywords. Optionally and preferably, such partitions and/or associations are identified by means of a clustering algorithm. Next, a particular subgroup of keywords is then selected from the entire group of keywords. This subgroup of keywords could optionally be associated according to the concept of "coffee" for example, such that all of the keywords in this subgroup would therefore all be related to this concept.

This particular selected subgroup of keywords, related to the concept of "coffee" for the purposes of this example, would then be used to partition the entire group of documents, in order to locate a subgroup of documents which are also related to the concept of "coffee". The process of partitioning the group of documents could also optionally and preferably be performed with a clustering algorithm, which in this example would use the metric of the number of times that each one of the keywords, that belong to the selected subgroup of keywords appeared in each document. Thus, the method of the present invention could optionally and preferably be used to partition documents into subgroups, by using a subgroup of keywords, or any other selected subgroup of characteristics.

In addition, other examples for use with the method of the present invention include, but are not limited to, financial data analysis and marketing analysis. Financial data analysis could optionally be performed with the method of the present invention by substituting stocks in some index, such as the Dow Jones, for the samples in the previous example with regard to genetics. The prices of these stocks at different times and/or the volume of trade and/or volatility of these stocks would then be used to substitute for the genes in the previous example for genetics. For marketing analysis, a list of potential customers for a particular company and/or product or service could optionally substitute for the samples in the previous genetic example. Some type of parameter or factor which characterizes these customers would then optionally substitute for the genes as in the previous genetic example. Examples of such a parameter or factor include, but are not limited to, the income of the customers, their previous record of purchases, and/or the record of browsing through the Internet. Appendix A This Appendix contains a simple example with artificial data, which illustrates some of the problems in the art which are solved by the method of the present invention. The data which were generated models the following situation. Two independent biological processes, $p_1$ and $p_2$ involve two different subsets of genes, $G_1$ and $G_2$ respectively. The number of genes in $G_1$ is much larger than the number of genes in $G_2$. Both processes have two phases: an active phase in which the corresponding genes are highly expressed, and an inactive phase in which the expression of these genes is suppressed. Every cell must be (simultaneously) in one of the phases of each process. Denote by $p_3$ a third process, one that influences only those cells which are in the active phase of the $p_1$ process. The process $p_3$ involves a third set of genes, $G_3$, which can be either activated or suppressed. The variation in the expression levels of genes which are unaffected by either process is due to noise. This situation is summarized in Table 1.

| Process | Genes | Samples in active phase | Samples in inactive phase | Remarks |
|---|---|---|---|---|
| $p_1$ | $G_1$ (1–20) | 1–5 | 6–10 | |
| $p_2$ | $G_2$ (21–25) | 1, 2, 8–10 | 3–7 | |
| $p_3$ | $G_3$ (26–30) | 3–5 | 1, 2 | $p_3$ acts only in cells in active phase of $p_1$. |
| | $G_4$ (31–130) | | | Genes that take no part in either process. |

Figure 15:
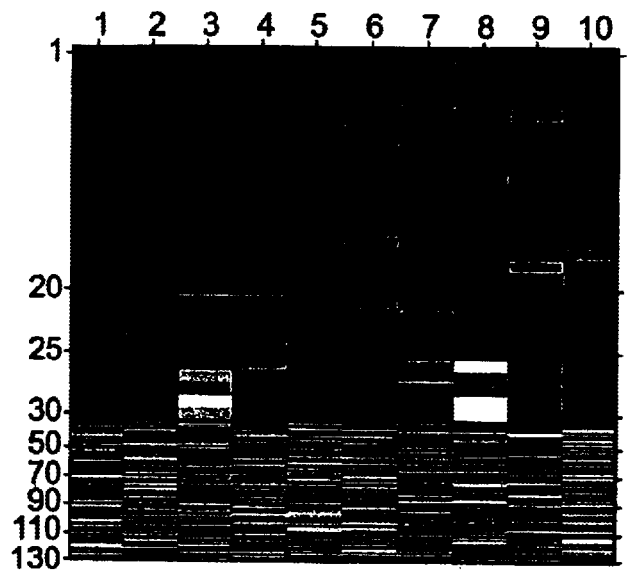
FIG. 15 shows an expression level matrix for the motivation example. A lighter shade indicates a higher expression level. See text for details.

FIG. 15 shows an expression level matrix $A_{ij}$ for the situation just described, with $|G_1|=20$, $|G_2|=|G_3|=5$ and $|G_4|=100$. Samples 1 through 5 are in the active phase of $p_1$; the high expression levels of the $G_1$ genes in these samples are represented by lighter shades of gray. The same group of genes are suppressed in samples 6–10(dark-shades of gray). Samples 1, 2 and 8 through 10 are in the active phase of process $p_2$. Only samples 1 through 5 can be affected by $p_3$: the first two are in the inactive phase of this process. Note that a large majority of the genes, $G_4$, do not participate in either process. When the samples are clustered using the expression levels of all the genes, the group $G_4$ introduces an effective and realistic amount of noise.

The only classification of the samples which rises above this noise is that into the two different phases of $p_1$. Partition of the samples according to their participation in the "weak" processes $p_2$ and $p_3$ is completely obscured. On the other hand, clustering the genes (on the basis of data from all samples) produces three clear clusters, containing $G_1$, $G_2$ and $G_3$ respectively, with the genes of $G_4$ constituting a dilute background.

$$d_{ik} = \left[\sum_{j=1}^{130} (A_{i,j} - A_{k,j})^2\right]^{1.2}$$

Figure 15A:
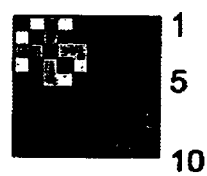
Figure 15B:
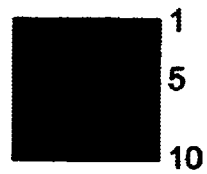
Figure 15C:
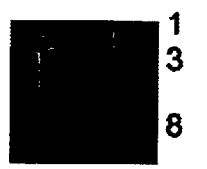

The manner in which the samples are partitioned can be seen clearly by inspecting the matrix of distances between them, calculated over all the genes, shown in FIG. 15(a). Samples 1–5 appear to be at relatively small distances from each other, whereas the other five form a more dilute "background". This distance matrix is to be compared with those matrices obtained by using only genes from $G_1$ and from $G_2$ (FIGS. 15(b) and (c), respectively). In the first matrix, two well separated dense clusters of samples 1–5 and 6–10 are seen, whereas the second matrix partitions the samples according to the process $p_2$; note that samples 1, 2 are at a small distance from each other and from samples 8–10, but far from the group of samples 3–7 (which are close to each other).

Figure 15D:
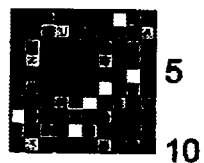
Figure 15E:
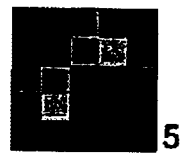

Only the genes of $G_3$ are considered, and all samples are clustered. Samples 1, 2 may be anticipated to be located in one cluster and 3–5 in another cluster; in fact, the result is a single cluster, which includes all genes. This is caused by the fact that samples 6–10, which are not affected by $p_3$, link the samples of the two expected groups (see FIG. 15(d)). If, however, only the samples 1–5 are clustered, the corresponding upper left corner of FIG. 15(d) provides a clear separation to the two expected groups of samples.

This example demonstrates the need for the method according to the present invention. The gene clusters $G_1$ are identified first and are used to partition the samples: this partition can then be used further, to reveal the inner structure of a cluster.

The problems presented in this illustrative but artificial example occur in real data as well. In real gene expression data, a group of genes which participate in a particular biological process can be expected to exhibit correlated expression patterns over the samples and to form a cluster. When only the members of this cluster are used to represent the different samples, partition of the samples to those samples in which this process does occur, from those samples in which it does not occur, should become easier. Furthermore, when this cluster of samples is identified, the problem of identifying its sub-structure becomes easier.

In addition, as previously described, clustering analysis which is performed by using select subsets of real data actually reveals important features which were hidden when the full data set was used.

While the invention has been described with respect to a limited number of embodiments, it will be appreciated that many variations, modifications and other applications of the invention may be made

What is claimed is:

1. A method for partitioning a first plurality of objects and a second plurality of objects, each of the first plurality of objects being related to at least one of the second plurality of objects according to at least one characteristic of each object, the method being performed by a data processor, the method comprising:

partitioning the first plurality of objects into a first plurality of object subsets according to a subset of the second plurality of objects; and partitioning the second plurality of objects according to a subset of the first plurality of objects to form a second plurality of object subsets, such that said partitioning of the second plurality of objects is coupled to said partitioning of the first plurality of objects and wherein said first and second plurality of objects are partitioned in an unsupervised manner.

2. The method of claim 1, wherein a subset of the first plurality of objects comprises the entirety of the first plurality of objects.

3. The method according to claim 1, wherein said partitioning of the first plurality of objects comprising:

applying a clustering algorithm on the first plurality of objects according to said at least one characteristic to form a plurality of object subsets; and detecting at least one stable cluster from said plurality of object subsets.

4. The method of claim 3, wherein said clustering algorithm is the superparamagnetic clustering algorithm.

5. The method of any of claim 1, wherein the method is repeated until no additional subgroups are detected.

6. The method of claim 5, wherein no additional subgroups are detected for both the first plurality of objects and the second plurality of objects.

7. The method of claim 1, wherein said partitioning of the first plurality of objects is performed by partitioning a plurality of subset groups of the first plurality of objects according to a known classification.

8. The method of claim 1, further comprising:

analyzing each group of said at least two groups of the second plurality of objects by comparing said group of said at least two groups of the second plurality of objects to an entirety of the second plurality of objects to determine if said group is differentiated from the second plurality of objects.

9. The method of claim 1, further comprising:

analyzing each subset of the first plurality of objects by comparing said subset of the first plurality of objects to an entirety of the first plurality of objects to determine if said subset is differentiated from the first plurality of objects.

10. The method of claim 8, wherein the analysis is performed according to a statistical test for similarity.

11. The method of any of claim 8, wherein the first plurality of objects is normalized before being portioned.

12. The method of any of claim 8, wherein the second plurality of objects is normalized before being partitioned.

13. The method of any of claim 1, wherein the first plurality of objects are genes and the second plurality of objects are samples for being analyzed according to a characteristic of said genes.

14. The method of claim 13, wherein said samples are characterized according to expression levels of said genes.

15. The method of claim 13, wherein said genes forming a cluster characterize a pathological state of a plurality of subjects, said samples being obtained from said plurality of subjects.

16. The method of any of claim 13, wherein said genes forming a cluster participate together in a biological process.

17. The method of any of claim 13, wherein said genes are characteristic of samples taken from subjects having a cancerous condition.

18. The method of claim 17, wherein at least one characteristic of said genes partitions said samples according to a type of cancer in said cancerous condition.

19. The method of claim 18, wherein said at least one characteristic of said genes is an expression profile of said genes.

20. The method of claim 19, wherein said expression profile is determined as an expression matrix, such that the division of said samples into subgroups according to said expression profile for said genes is performed with said expression matrix.

21. The method of claim 18, wherein said at least one characteristic of said genes is an effect of treatment on said subjects.

22. A method for separating at least one of a first plurality of objects and a second plurality of objects into at least two groups, each of the first plurality of objects being related to at least one of the second plurality of objects, the method being performed by a data processor, the method comprising: dividing the first plurality of objects into a first plurality of object subsets; and partitioning the second plurality of objects according to at least one of said first plurality of object subsets to form at least two groups of the second plurality of objects, wherein the first plurality of objects are keywords and the second plurality of objects arc documents containing said keywords.

23. The method of claim 1, wherein a natural separation exists within at least one of the first plurality of objects and of the second plurality of objects.

24. A method for selecting a second plurality of objects according to a first plurality of objects, each of the first plurality of objects being related to at least one of the second plurality of objects according to at least one characteristic of each object, the method being performed by a data processor, the method comprising:

partitioning the first plurality of objects into a plurality of first object subsets according to at least one characteristic of the first plurality of objects;

partitioning the second plurality of objects according to each one of said plurality of first object subsets to form a subgroup of the second plurality of objects according to each one of said plurality of first object subsets; and comparing each subgroup of the second plurality of objects to every other subgroup of the second plurality of objects, such that said partitioning of the second plurality of objects is coupled to said partitioning of the first plurality of objects.

25. A method for selecting a second plurality of biological objects from a collection of biological objects according to a first plurality of biological objects, each of the first plurality of objects being related to at least one of the second plurality of objects according to at least one characteristic of each object, wherein the relationship is known from data about the objects, the method being performed by a data processor, the method comprising:

partitioning the first plurality of objects into a plurality of first object subsets according to at least one characteristic of the first plurality of objects;

selecting the second plurality of objects according to each one of said plurality of first object subsets from the collection of objects; and comparing the second plurality of objects to every other subgroup of the collection of objects, such that said selecting of the second plurality of objects is coupled to said partitioning of the first plurality of objects in an unsupervised manner.

26. The method of claim 25, wherein said partitioning and said selecting are performed repeatedly until no additional stable partitions are obtained for at least one of said first or said second plurality of objects.

27. The method of claim 1, wherein a subset of the second plurality of objects comprises the entirety of the second plurality of objects.

* * * * *

UNITED STATES PATENT AND TRADEMARK OFFICE
CERTIFICATE OF CORRECTION

PATENT NO. : 6,965,831 B2
DATED : November 15, 2005
INVENTOR(S) : Eytan Domany et al.

It is certified that error appears in the above-identified patent and that said Letters Patent is hereby corrected as shown below:

Column 24,
Line 4, change "portioned" to -- partitioned --.

Signed and Sealed this

Fourth Day of April, 2006

JON W. DUDAS
*Director of the United States Patent and Trademark Office*